US010347378B2

(12) United States Patent
Okabe et al.

(10) Patent No.: US 10,347,378 B2
(45) Date of Patent: Jul. 9, 2019

(54) MEDICAL SUPPORT APPARATUS, OPERATION METHOD OF MEDICAL SUPPORT APPARATUS, AND MEDICAL SUPPORT SYSTEM

(71) Applicant: FUJIFILM Corporation, Tokyo (JP)

(72) Inventors: Yuki Okabe, Tokyo (JP); Yasuyo Nenoki, Tokyo (JP); Yasunori Ohta, Tokyo (JP); Hiroshi Hiramatsu, Tokyo (JP); Tsuyoshi Hirakawa, Tokyo (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 677 days.

(21) Appl. No.: 15/010,516

(22) Filed: Jan. 29, 2016

(65) Prior Publication Data

US 2016/0224737 A1 Aug. 4, 2016

(30) Foreign Application Priority Data

Jan. 30, 2015 (JP) ................................. 2015-017945

(51) Int. Cl.
*G16H 40/20* (2018.01)
*G16H 40/63* (2018.01)
*G06F 19/00* (2018.01)

(52) U.S. Cl.
CPC ............. *G16H 40/20* (2018.01); *G06F 19/00* (2013.01); *G16H 40/63* (2018.01)

(58) Field of Classification Search
CPC ........... G06F 17/60; G06F 17/00; G09G 5/34; G06Q 10/0633; G16H 15/00
USPC ........................... 705/2, 3; 345/684; 715/255
See application file for complete search history.

(56) References Cited

U.S. PATENT DOCUMENTS

| | | | | |
|---|---|---|---|---|
| 7,456,850 | B2 * | 11/2008 | Meier | G06F 3/04812 345/157 |
| 2004/0249676 | A1 * | 12/2004 | Marshall | G06Q 10/10 705/2 |
| 2008/0021738 | A1 * | 1/2008 | Komiya | G06Q 10/10 705/3 |

(Continued)

FOREIGN PATENT DOCUMENTS

JP 2006-338521 A 12/2006

OTHER PUBLICATIONS

Google patents search, Aug. 15, 2018 (Year: 2018).*
Google patents search, Aug. 15, 2018.*

*Primary Examiner* — Dilek B Cobanoglu
(74) *Attorney, Agent, or Firm* — Sughrue Mion, PLLC

(57) ABSTRACT

In the case where a special icon disposed at an item of an examination is hidden, and a medical staff has not confirmed a medical report of various types of medical examinations whose progress statuses are represented by small icons of the special icon, an unconfirmed medical-care-process display section representing that there is a medical examination whose medical report has not been confirmed is displayed on a first display screen. The unconfirmed medical-care-process display section is obtained by arranging blocks each corresponding to the small icon representing the progress status of the medical examination whose medical report has not been confirmed, and the unconfirmed medical-care-process display section is inserted between the icons of patients arranged along the horizontal axis, and displayed.

18 Claims, 27 Drawing Sheets

(56) References Cited

U.S. PATENT DOCUMENTS

2012/0304054 A1* 11/2012 Orf ....................... G16H 15/00
715/255
2013/0317847 A1* 11/2013 Yui ....................... G06Q 50/22
705/2

* cited by examiner

FIG.7

FOR DOCTOR

| PATIENT ID | PATIENT TYPE | STAFF ID | DISEASE NAME | MEDICAL CARE PROCESS ITEM ||||||||
|---|---|---|---|---|---|---|---|---|---|---|
| | | | | S.H. | MEDICAL EXAM | R.A. | PRE. SUM. | A.S. | AG.A. | AG.S. |
| 0123456789 | P.S.S. | D001 D005 D018 D050 | 01/23 G.C. D001 | 01/23 09:30 1/25–1/30 ROOM 405: SINGLE | 01/24 DR:NOT-PERFORMED US:D050 UNCONFIRMED D001,D005,D018 CONFIRMED ES:CONFIRMED | 01/23 (G) D005 | 01/23 COMPLETED D001 | 01/23 01/28 14:30– D001 | 01/23 01/25 D005 | 01/23 01/23 D001 |
| 000003210 | P.S.S. | D002 D005 D007 D039 | 01/23 I.C. D002 | 01/23 09:30 1/25–1/31 ROOM 505: SINGLE | 01/24 CT,ECG:NOT-PERFORMED DR,ES:CONFIRMED US,BL:D007 UNCONFIRMED D002,D005,D039 CONFIRMED BIO:CONFIRMED | 01/23 (G) D005 | 01/20 NOT-COMPLETED SUSPENDED (A) D002 | 01/23 01/27 16:30– D002 | 01/23 NOT-COMPLETED AWAITING D002 | NOT-STARTED |
| 000264798 | P.S.S. | D003 D005 D027 D042 | 01/24 AP. D003 | 01/24 1/27–2/10 ROOM 503: 4 BEDS | 01/24 CT:NOT-PERFORMED BL,US:CONFIRMED | 01/24 (L) D005 | 01/25 COMPLETED D003 | 01/24 01/29 13:30– D003 | | 01/24 01/24 D003 |

| STAFF ID | DIAGNOSTIC IMAGE | MEDICAL REPORT |
|---|---|---|
| 0123456789 | I:¥0123456789¥DR¥20140802¥DR001 | RE:¥0123456789¥¥201400802¥RE001 |
| | I:¥0123456789¥DR¥20140808¥DR009 | RE¥0123456789¥¥201400809¥RE007 |
| | ⋮ | ⋮ |

| PATIENT TYPE | MEDICAL STAFF TYPE | ITEM |
|---|---|---|
| P.S.S. | DOCTOR | DISEASE NAME, SCHEDULING OF HOSPITALIZATION, MEDICAL EXAMINATION, REQUEST FOR ANESTHESIA, PREOPERATIVE SUMMARY, APPLICATION FOR SURGERY, AGREEMENT TO ANESTHESIA, AGREEMENT TO SURGERY |
| | LABORATORY TECHNOLOGIST | DISEASE NAME, SCHEDULING OF HOSPITALIZATION, MEDICAL EXAMINATION, REQUEST FOR ANESTHESIA, PREOPERATIVE SUMMARY, APPLICATION FOR SURGERY |
| | NURSE | DISEASE NAME, SCHEDULING OF HOSPITALIZATION, MEDICAL EXAMINATION, REQUEST FOR ANESTHESIA, PREOPERATIVE SUMMARY, APPLICATION FOR SURGERY, AGREEMENT TO ANESTHESIA, AGREEMENT TO SURGERY |
| | DIETICIAN | |
| OUTPATIENT | DOCTOR | DISEASE NAME, MEDICAL EXAMINATION, PATIENT REFERRAL |
| | LABORATORY TECHNOLOGIST | DISEASE NAME, MEDICAL EXAMINATION, PATIENT REFERRAL |
| | NURSE | DISEASE NAME, MEDICAL EXAMINATION, PATIENT REFERRAL |
| | DIETICIAN | |
| INPATIENT | DOCTOR | DISEASE NAME, MEAL, SCHEDULING OF HOSPITALIZATION, MEDICAL EXAMINATION, APPLICATION FOR SURGERY, CLINICAL PATH, PRESSURE ULCER MANAGEMENT PLAN, NUTRITIONAL MANAGEMENT PLAN, THERAPEUTIC PLAN FOLLOWING HOSPITAL DISCHARGE, HOSPITAL DISCHARGE SUMMARY |
| | LABORATORY TECHNOLOGIST | DISEASE NAME, MEAL, SCHEDULING OF HOSPITALIZATION, MEDICAL EXAMINATION, APPLICATION FOR SURGERY |
| | NURSE | DISEASE NAME, MEAL, SCHEDULING OF HOSPITALIZATION, MEDICAL EXAMINATION, APPLICATION FOR SURGERY, CLINICAL PATH, PRESSURE ULCER MANAGEMENT PLAN, NUTRITIONAL MANAGEMENT PLAN, THERAPEUTIC PLAN FOLLOWING HOSPITAL DISCHARGE |
| | DIETICIAN | DISEASE NAME, MEAL, SCHEDULING OF HOSPITALIZATION, MEDICAL EXAMINATION, APPLICATION FOR SURGERY, CLINICAL PATH, NUTRITIONAL MANAGEMENT PLAN, THERAPEUTIC PLAN FOLLOWING HOSPITAL DISCHARGE |

FIG.19

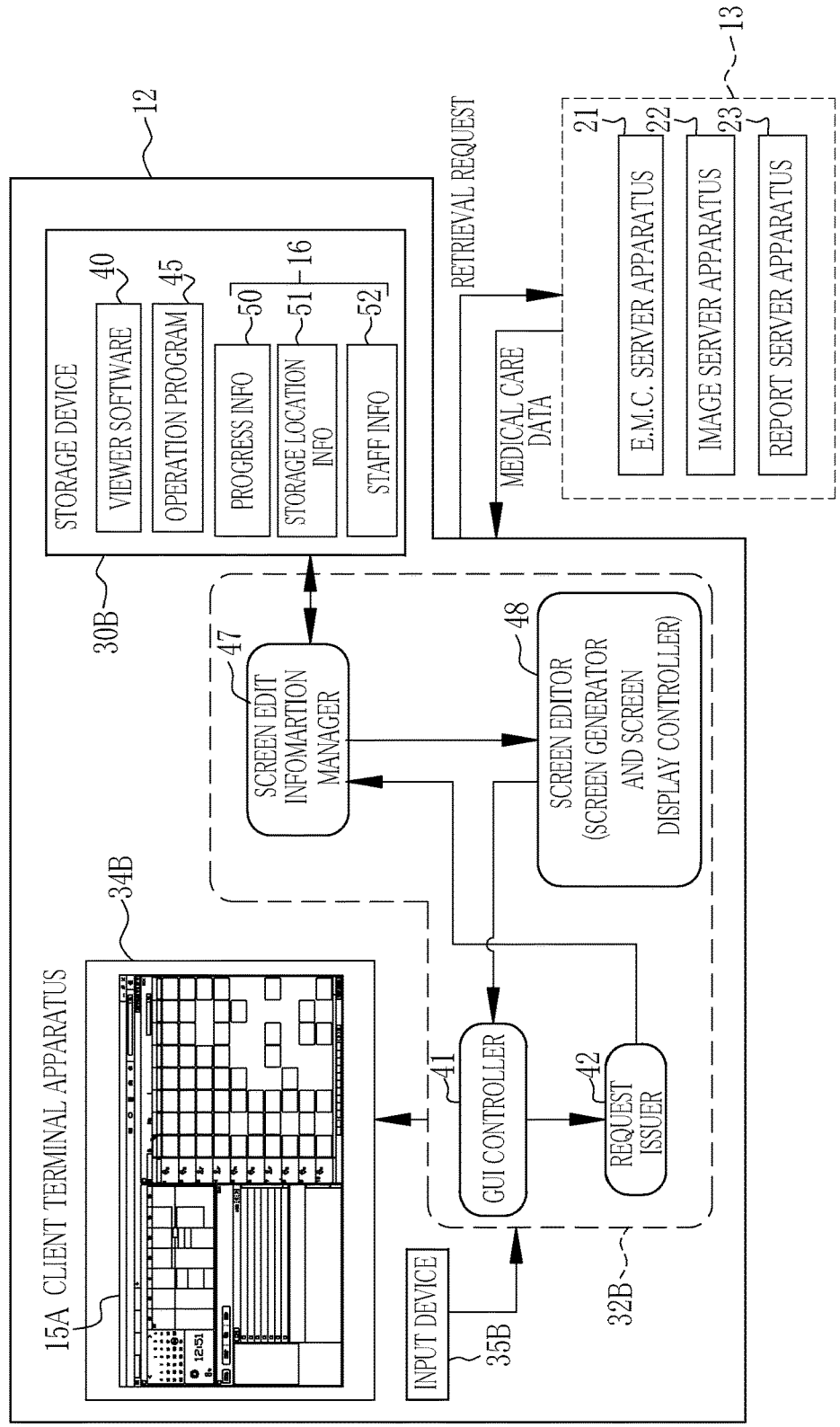

MEDICAL SUPPORT APPARATUS, OPERATION METHOD OF MEDICAL SUPPORT APPARATUS, AND MEDICAL SUPPORT SYSTEM

CROSS-REFERENCE TO RELATED APPLICATIONS

The present application claims priority under 35 U.S.C. § 119 to Japanese Patent Application No. 2015-017945, filed Jan. 30, 2015. The above application is hereby expressly incorporated by reference, in its entirety, into the present application.

BACKGROUND OF THE INVENTION

1. Field of the Invention

The present invention relates to a medical support apparatus, an operation method of a medical support apparatus, and a medical support system.

2. Description Related to the Prior Art

In medical fields, in order to smoothly perform medical treatment on a patient by a medical staff such as a doctor who diagnoses and treats the patient and a laboratory technologist who performs a medical examination on the patient, a patient list for displaying a plurality of items on a patient-by-patient basis is generated in a two-dimensional area, in which items representing a plurality of medical care processes such as medical examinations and medical tests performed on a patient by medical staffs, and patient identification information for identifying a plurality of patients are arranged, such that the generated patient list is viewed by a medical staff.

For example, Japanese Patent Laid-Open Publication No. 2006-338521 discloses a medical support apparatus (referred to as "management server" in this document) for generating a display screen having a patient list, in which the items are arranged along a horizontal axis and the patient identification information (referred to as "patient numbers" in this document) are arranged along a vertical axis. The medical support apparatus outputs the generated display screen to a client terminal apparatus, which is operated by the medical staff. The client terminal apparatus displays the display screen on a display panel, which is viewed by each medical staff.

According to Japanese Patent Laid-Open Publication No. 2006-338521, items of ophthalmology as a medical test including a vision test, mydriasis, fundus imaging, non-contact intraocular pressure measurement, and items of medical care processes other than the medical test including consultation, treatment, and accounting are exemplified. Each of these items is assigned with an icon (referred to as a status mark in this document) representing a progress status of the medical care process.

The icons display multiple types of progress statuses such as "reservation", "reception", "examination", "suspended", "unconfirmed", and "confirmed". The icons are distinguished from one another by different shapes (circle, triangle, rectangle, and the like) filled with color in different levels, changes in shape and color of the icons, and graphics for easy visual comprehension. The progress status "unconfirmed" corresponds to a state in which the medical staff has not confirmed a result of the medical care process such as a test result of the medical test, and the progress status "confirmed" corresponds to a state in which the medical staff has confirmed the result of the medical care process.

According to Japanese Patent Laid-Open Publication No. 2006-338521, some of the items described above are displayed on the display screen, but others which cannot be contained within the display screen are not displayed (i.e., hidden). A horizontal scroll bar is provided in the patient list so as to make it possible to display the hidden items and hidden icons disposed at the hidden items (i.e., hidden sections).

As well known, the scroll bar has a slider movable in the scroll bar, and a pair of arrow buttons disposed to both ends of the scroll bar. The hidden sections are allowed to be displayed by a scrolling operation, such as operation of the slider or the arrow button with use of a mouse cursor, or rotation of a wheel button of a mouse.

A display mode, in which the hidden sections are allowed to be displayed by the scrolling operation in the case where a plurality of items constituting the patient list cannot be contained within the display screen and hidden, has been conventional, as disclosed in Japanese Patent Laid-Open Publication No. 2006-338521.

However, according to such a display mode in which the scroll bar is provided, the hidden sections are not displayed unless the scrolling operation is performed. As a result, in the case where the icon disposed at the item representing the medical care process whose result is required to be confirmed by the medical staff, such as the item of the medical test, is hidden, as disclosed in Japanese Patent Laid-Open Publication No. 2006-338521, it is not until the scrolling operation is performed that the progress status is displayed with use of the icon in the hidden section and noticed by a medical staff. Therefore, in some cases, the medical staff may not notice the existence of "unconfirmed" medical care process, such that the medical care process remains to be suspended and never ends.

SUMMARY OF THE INVENTION

In view of the foregoing problems, an object of the present invention is to provide a medical support apparatus capable of surely preventing display of a progress status of a medical care process from being missed due to an icon, an operation method of the medical support apparatus, and a medical support system.

In order to achieve the above and other objects and advantages of the present invention, a medical support apparatus of the present invention includes a screen generator and a screen display controller. The screen generator is configured to generate a display screen having a patient list in which icons are arranged in a matrix in a two-dimensional area with an item arrangement axis and a patient identification information arrangement axis. A plurality of medical care processes performed on patients by medical staffs are arranged as items in the item arrangement axis, and patient identification information for identifying the patients are arranged in the patient identification information arrangement axis. The icons represent progress statuses of the medical care processes on a patient-by-patient basis. The screen display controller is configured to allow part of the items and the icons disposed at the part of the items, which are not contained within the display screen and hidden, to be displayed by a scrolling operation. The screen display controller displays an unconfirmed medical-care-process display section representing that there is an unconfirmed medical care process on the display screen in the case where there is the icon corresponding to the unconfirmed medical care process whose result has not been confirmed by the medical staff among the hidden icons.

The unconfirmed medical-care-process display section is preferably obtained by arranging blocks corresponding the icons representing the progress statuses of the unconfirmed medical care processes. The unconfirmed medical-care-process display section is preferably inserted between the icons of patients arranged along the item arrangement axis, and displayed. The blocks are preferably aligned and displayed at a head position of the items at a side in which the patient identification information are arranged.

It is preferable that the medical care process which is required to be confirmed is a medical examination. In this case, the unconfirmed medical-care-process display section is preferably displayed in the case where a preliminarily-set time limit has been reached after a result of the medical examination or a medical report as a reporting of the result of the medical examination is uploaded but the result of the medical examination or the medical report has not been confirmed. The medical examination is preferably at least one of imaging examination, laboratory test, and physiological test.

The icon is preferably displayed only for the medical care process scheduled to be performed.

It is preferable that the patient list is generated according to the medical staffs, and at least one of the item to be displayed, the patient identification information, and the progress status in the patient list varies according to the patients taken care of by the medical staffs and the medical care processes.

It is preferable that the patient list is generated according to patient types, and at least one of the item to be displayed, the patient identification information, and the progress status in the patient list varies according to the patient types. The patient types preferably include a patient scheduled for surgery who is scheduled to have surgery, an outpatient who visits a medical facility, and an inpatient who is admitted to the medical facility.

An operation method of a medical support apparatus of the present invention includes a screen generating step and a screen display controlling step. The screen generating step generates a display screen having a patient list in which icons are arranged in a matrix in a two-dimensional area with an item arrangement axis and a patient identification information arrangement axis. A plurality of medical care processes performed on patients by medical staffs are arranged as items in the item arrangement axis, and patient identification information for identifying the patients are arranged in the patient identification information arrangement axis. The icons represent progress statuses of the medical care processes on a patient-by-patient basis. The screen display controlling step allows part of the items and the icons disposed at the part of the items, which are not contained within the display screen and hidden, to be displayed by a scrolling operation. The screen display controlling step displays an unconfirmed medical-care-process display section representing that there is an unconfirmed medical care process on the display screen in the case where there is the icon corresponding to the unconfirmed medical care process whose result has not been confirmed by the medical staff among the hidden icons.

A medical support system of the present invention is composed of a medical support apparatus, a client terminal apparatus, and a network that connects the medical support apparatus and the client terminal apparatus in a communicable manner. The medical care support system includes a screen generator and a screen display controller. The screen generator is configured to generate a display screen having a patient list in which icons are arranged in a matrix in a two-dimensional area with an item arrangement axis and a patient identification information arrangement axis. A plurality of medical care processes performed on patients by medical staffs are arranged as items in the item arrangement axis, and patient identification information for identifying the patients are arranged in the patient identification information arrangement axis. The icons represent progress statuses of the medical care processes on a patient-by-patient basis. The screen display controller is configured to allow part of the items and the icons disposed at the part of the items, which are not contained within the display screen and hidden, to be displayed by a scrolling operation. The screen display controller displays an unconfirmed medical-care-process display section representing that there is an unconfirmed medical care process on the display screen in the case where there is the icon corresponding to the unconfirmed medical care process whose result has not been confirmed by the medical staff among the hidden icons.

According to the present invention, in the case where there is the icon corresponding to the unconfirmed medical care process whose result has not been confirmed by the medical staff among the hidden icons, the unconfirmed medical-care-process display section, which represents that there is the unconfirmed medical care process, is displayed on the display screen. Therefore, it is possible to provide the medical support apparatus capable of surely preventing the display of the progress status of the medical care process from being missed due to the icon, the operation method of the medical support apparatus, and the medical support system.

BRIEF DESCRIPTION OF THE DRAWINGS

The above objects and advantages of the present invention will become more apparent from the following detailed description when read in connection with the accompanying drawings, in which:

FIG. 7 illustrates the content of progress status information;

FIG. 9 illustrates the content of storage location information;

FIG. 15 illustrates the content of an item list organized according to patient types and medical staff types;

FIG. 19 illustrates a second display screen;

FIG. 27 is a block diagram illustrating an example in which the client terminal apparatus has a function of a medical support apparatus.

DETAILED DESCRIPTION OF THE PREFERRAL EMBODIMENT(S) OF THE PRESENT INVENTION

First Embodiment

Figure 1:
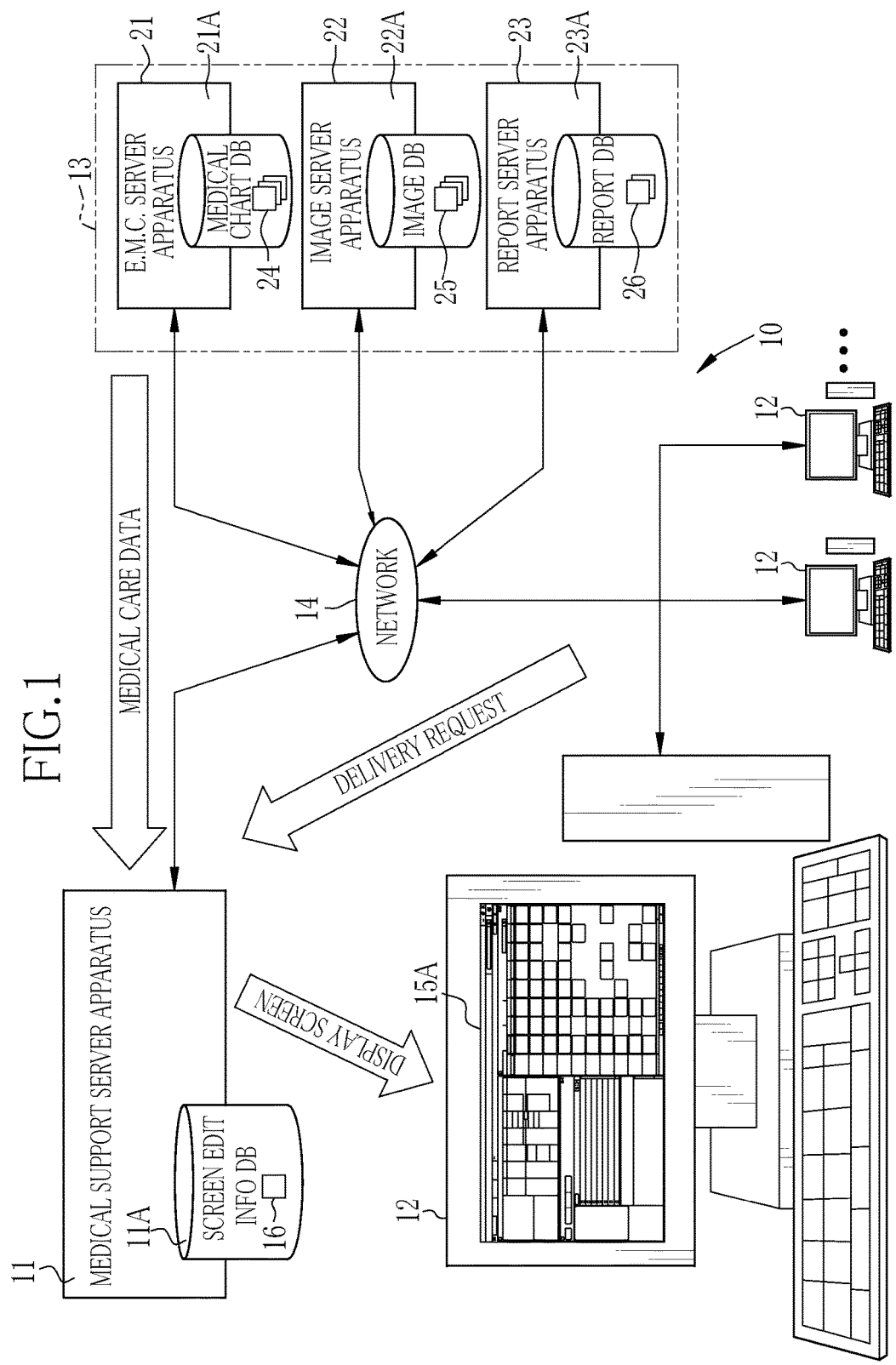
FIG. 1 is an explanatory view illustrating a medical support system.

In FIG. 1, a medical support system 10 is a computer system that supports medical care in a medical facility such as a hospital. The medical support system 10 includes a medical support server apparatus 11, a client terminal apparatus 12, and a server cluster 13, which are connected to one another in a communicable manner through a network 14 such as a LAN (Local Area Network) provided in the medical facility.

The medical support server apparatus 11 functions as a medical support apparatus according to an aspect of the present invention. To be more specific, the medical support server apparatus 11 retrieves medical care data, which is obtained during a medical care process of a patient, from the server cluster 13, and generates a first display screen 15A (which is an example of a display screen, see FIG. 11) and a second display screen 15B (see FIG. 19) based on the retrieved medical care data. The medical support server apparatus 11 delivers the generated first display screen 15A and second display screen 15B to the client terminal apparatus 12. Incidentally, FIG. 1 illustrates the first display screen 15A.

The medical support server apparatus 11 includes a screen edit information database (DB) 11A in which screen edit information 16 is stored. The medical support server apparatus 11 refers to the screen edit information 16 to generate or edit the first display screen 15A and the second display screen 15B.

The client terminal apparatus 12 is disposed in each clinical department in the medical facility, such as internal medicine, surgery, otolaryngology, and ophthalmology, and in each laboratory department such as radiological examination department and clinical examination department. The client terminal apparatus 12 is operated by the medical staff such as a doctor of a clinical department, a laboratory technologist of a laboratory department, a nurse, or a dietician. The client terminal apparatus 12 displays the first display screen 15A and the second display screen 15B, which are transmitted from the medical support server apparatus 11, to be viewed by the medical staff. In other words, the client terminal apparatus 12 functions as a viewer terminal, which is used by the medical staff to view the first display screen 15A and the second display screen 15B.

The medical support server apparatus 11 delivers the first display screen 15A and the second display screen 15B in, for example, XML data format, which is described by a markup language such as XML (Extensible Markup Language), through the web to the client terminal apparatus 12. Based on the XML data, the client terminal apparatus 12 reproduces and displays the first display screen 15A and the second display screen 15B on the web browser. Incidentally, another data description language such as JSON (JavaScript (registered trademark) Object Notation) may be used instead of XML.

The server cluster 13 retrieves the medical care data in accordance with a retrieval request, which is a request to retrieve medical care data, from the medical support server apparatus 11, and transmits the retrieved medical care data to the medical support server apparatus 11. The server cluster 13 includes an electronic medical chart server apparatus 21, an image server apparatus 22, and a report server apparatus 23.

The electronic medical chart server apparatus 21 includes a chart database (DB) 21A, in which an electronic medical chart 24 is stored. ("Electronic medical chart" is abbreviated as E.M.C. in the drawings but fully displayed the actual screen.) Each of the consultation record data, test data, measurement data, order data, treatment record data, and accounting data is inputted as the medical care data to the electronic medical chart 24. In the consultation record data, the descriptions of consultation and diagnosis, the disease name, and the like are recorded. The test data includes test values of medical examinations such as laboratory test (e.g. blood test, biochemical test, and the like) and physiological test (e.g. electrocardiogram, electroencephalogram, and the like). The measurement data includes measurements of vital signs such as heart rate, pulse rate, blood pressure, body temperature, and the like of a patient. In the order data, various types of orders (requests) for medical examinations, creation of reports, treatments, surgery (operation), medication, and the like are recorded. In the treatment record data, events throughout the medical care processes of a patient (e.g. first consultation, hospital admission (hospitalization), hospital discharge, hospital readmission, treatments, surgery, medication, and complete cure) are recorded. In the accounting data, consultation and treatment fee, medication fee, hospital admission fee, and the like are recorded. Each of the above-described medical care data of the electronic medical chart 24 can be inputted and viewed through the client terminal apparatus 12.

The image server apparatus 22 is a so-called PACS (Picture Archiving and Communication System) server, and includes an image database (DB) 22A, in which a diagnostic image 25 is stored. The examples of the diagnostic images 25 include images captured in various types of imaging examinations such as CT (Computed Tomography) examination, MRI (Magnetic Resonance Imaging) examination, plain radiography examination, ultrasound examination, endoscopy examination, and the like. For example, the diagnostic image 25 is generated in a data file format like DICOM (Digital Imaging and Communications in Medicine) standard. The diagnostic image 25 can be viewed through the client terminal apparatus 12.

The report server apparatus 23 has a report DB 23A in which a medical report 26 is stored. The medical report 26 describes interpretation of the diagnostic image 25 by a radiological doctor, which is captured in the imaging examination. The medical report 26 can be generated and viewed through the client terminal apparatus 12.

Figure 2:
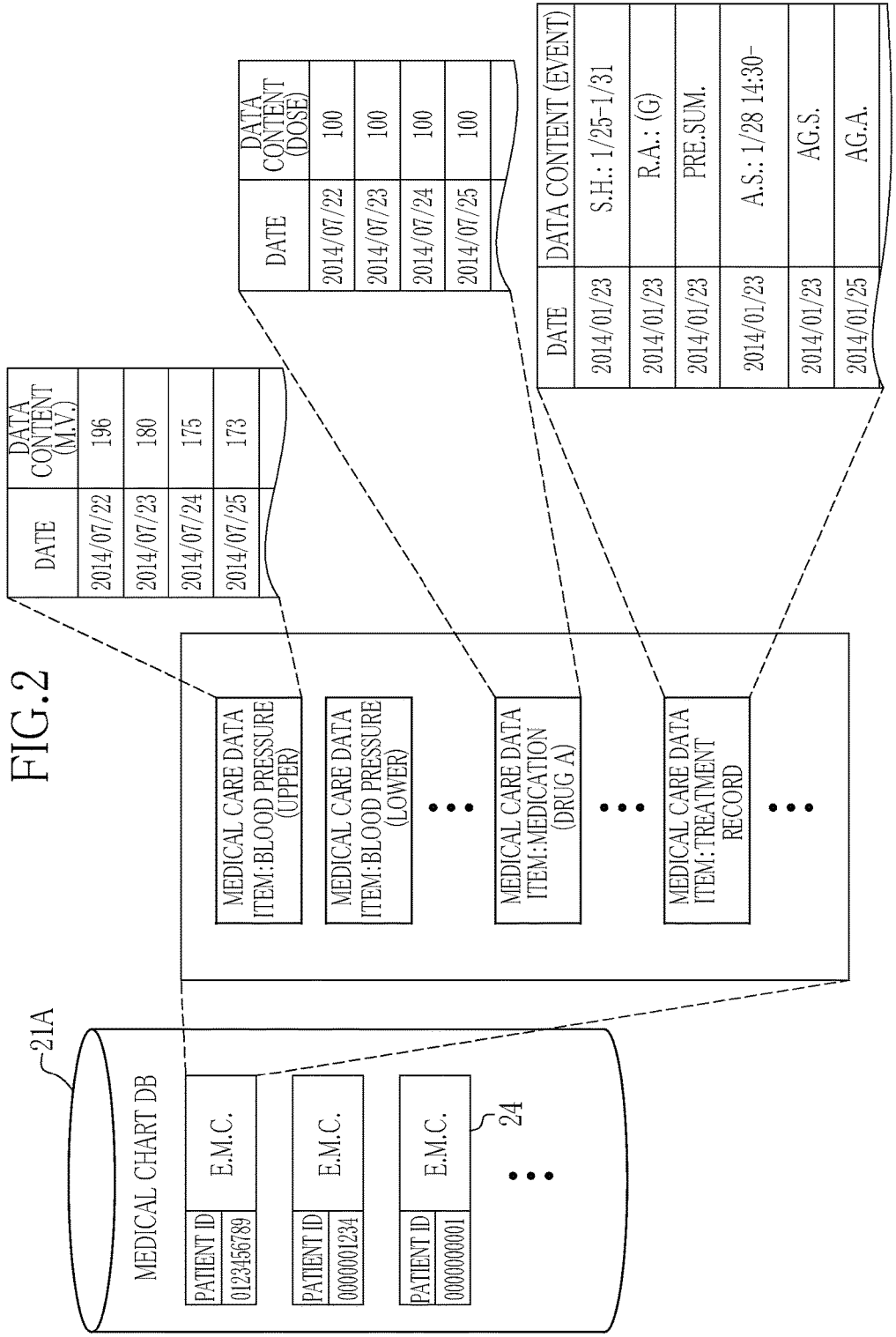
FIG. 2 illustrates descriptions of electronic medical charts stored in a chart DB.
Figure 3:
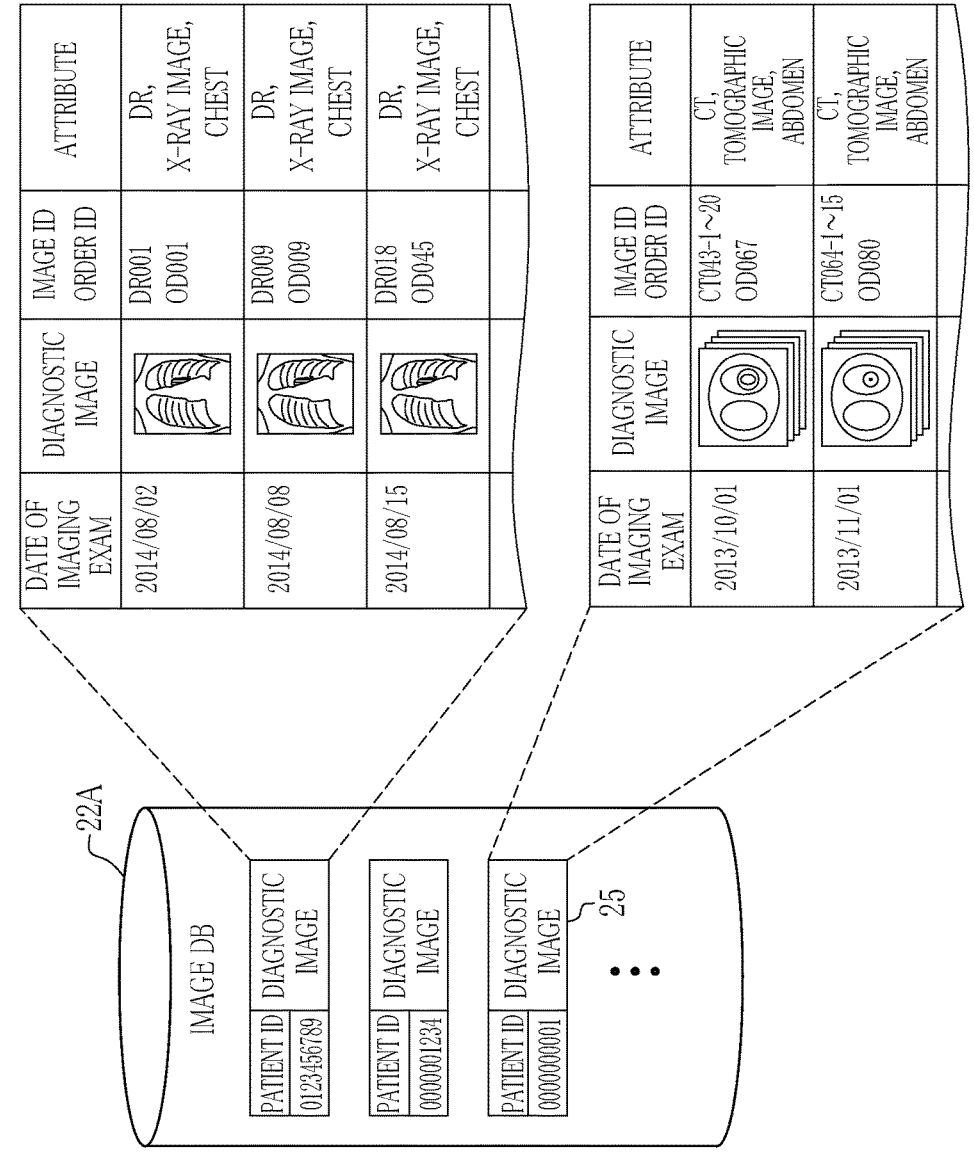
FIG. 3 illustrates contents of diagnostic images stored in an image DB.
Figure 4:
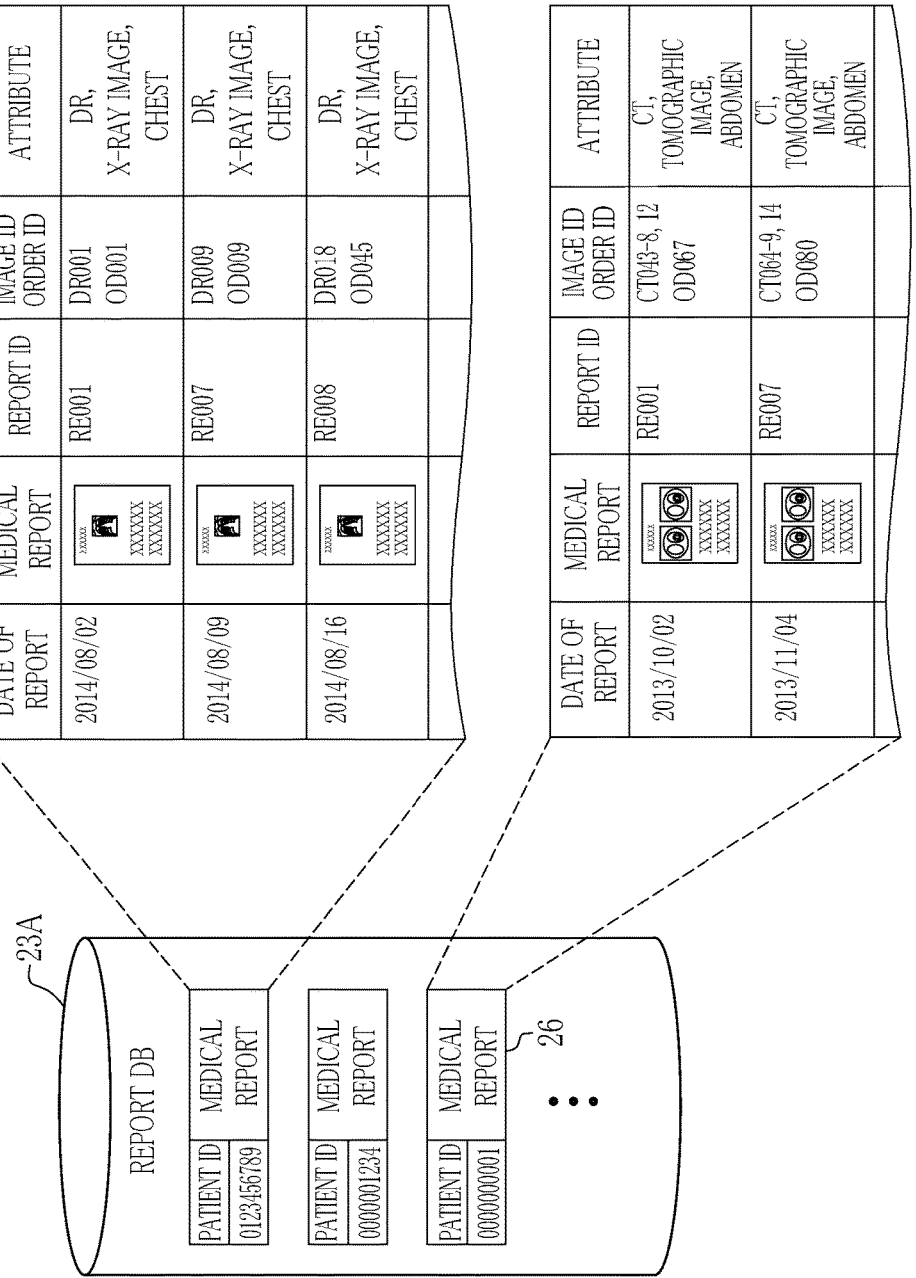
FIG. 4 illustrates descriptions of medical reports stored in a report DB.

In association with each of the electronic medical chart 24, the diagnostic image 25, and the medical report 26, a corresponding patient ID (Identification Data) and the like are stored as supplementary information (see FIGS. 2 to 4). The patient ID is composed of, for example, numbers and/or characters that identify a patient. A medical staff ID (shown as "staff ID" in the drawings) of a medical staff who inputted the medical care data is stored as the supplementary information in association with the electronic medical chart 24. The medical staff ID of a laboratory technologist who carried out the test is stored as the supplementary information in association with the diagnostic image 25. The medical staff ID of a radiological doctor who created the medical report 26 is stored as the supplementary information in association with the medical report 26. The medical staff ID shows which medical staff has performed the medical care process. Incidentally, a medical staff ID is composed of, for example, numbers and/or characters that identify a medical staff. The supplementary information such as the patient ID may be used as a search keyword to retrieve the corresponding electronic medical chart 24, diagnostic image 25, and medical report 26 from the respective DBs 21A, 22A, and 23A.

In FIG. 2, the electronic medical chart 24, which is stored in the chart DB 21A, is associated with the corresponding patient ID, which is a 10-digit number such as "0123456789", and managed on a patient-by-patient basis. In addition to the patient ID, the patient information, which includes the name, gender, the date of birth, age, and the like of the patient, and two or more items of medical care data are recorded in the electronic medical chart 24. The medical care data is arranged on an item-by-item basis such as "blood pressure (upper)", "blood pressure (lower)", "biochemical test A", and "treatment record" and stored chronologically. Incidentally, the medical care data includes the above-described consultation record data, the measurements of the vital signs (e.g. the heart rate, the pulse rate, the body temperature, and the like, in addition to the blood pressure), the order data, and the accounting data (not shown in FIG. 2).

A record of the items of the medical care data of one case includes information about dates and times of various events during the medical care process of the patient (e.g. dates and times of consultations, examinations, measurements, and medications (dates of medications or prescriptions)) and data descriptions (e.g. descriptions of diagnostic interview and diagnosis, the test value, the measurement value (abbreviated as "M.V." in the drawing, the same hereinafter), dose, medical fee, and descriptions of events). In the case of the item "medication", there may be a time lag between the administration of a drug and the onset of its clinical effect. For example, in the case where the medication in duration of a certain period (e.g. a predetermined dose per day for 5 days) is prescribed at a time, the dates and times on which the drug is to be taken are recorded as the "dates and times for medication".

The events recorded in the treatment record data include hospital admission (hospitalization), surgery, referral to another medical department, hospital discharge, hospital readmission, and the like. In the treatment record data, the description of the scheduling of hospitalization associated with the event "hospitalization", the description of the request for anesthesia associated with the event "surgery", the preoperative summary, the description of the application for the surgery, agreement to anesthesia, agreement to surgery, and the like are also recorded. Incidentally, the preoperative summary is a summary of the results of the medical examinations performed before the surgery. The agreement to anesthesia and the agreement to surgery are the forms that describe the necessity, the risks, and the like of the anesthesia and the surgery, and each form requires the signature or seal of the patient or his/her family.

In FIG. 3, the diagnostic image 25 stored in the image DB 22A is associated with the patient ID and managed on a patient-by-patient basis, in a manner similar to that of the electronic medical chart 24. In addition to the patient ID, the diagnostic image 25 is associated with attributes (supplementary information) such as the date and time of the imaging examination (the date and time of uploading the diagnostic image 25 to the image DB 22A), the image ID, the order ID, the type of the imaging examination (e.g. "plain radiography examination", "CT examination", or the like), the type of the diagnostic image ("X-ray image", "tomographic image", or the like), and the body part captured (e.g. "chest", "abdomen", or the like). The image server apparatus 22 transmits the diagnostic image 25 as the medical care data along with the supplementary information (the date and time and the attributes of the imaging examination) to the medical support server apparatus 11.

The image ID is composed of numbers and/or characters that identify a diagnostic image 25. The order ID is composed of numbers and/or characters that identify an order. In plain radiography, it is common that one X-ray image is captured per imaging examination. In CT examination, there are cases where two or more tomographic images are captured per imaging examination. In the case where two or more diagnostic images 25 are captured in one imaging examination, one order ID is provided to the diagnostic images 25 captured at a time so that the diagnostic images 25 are managed as a group. This applies the same to the plain radiography in the case where two or more X-ray images are captured in one imaging examination.

Incidentally, the supplementary information of the diagnostic image 25 may include the information about the position and the size of a lesion in the diagnostic image 25, the type of the lesion, a feature quantity of the lesion, the level of healing of the lesion, and the like. In a case where the ultrasound examination is performed as the imaging examination, the supplementary information may include a blood flow measurement, which is obtained by analyzing an ultrasonic image.

In FIG. 4, the medical report 26, which is stored in the report DB 23A, is associated with the patient ID and managed on a patient-by-patient basis, in a manner similar to the electronic medical chart 24 and the diagnostic image 25. The medical report 26 is associated with supplementary information that includes the patient ID, the date on which the medical report 26 is created (or the date on which the medical report 26 is uploaded to the report DB 23A), the report ID of the medical report 26, the image ID and the order ID of the diagnostic image 25 attached to the medical report 26, and the attributes similar to those of the diagnostic image 25. The report server apparatus 23 transmits the medical report 26 as the medical care data along with the supplementary information to the medical support server apparatus 11. Incidentally, in FIGS. 2 to 4, only the dates of the dates and times are displayed in the drawings but the dates and times are fully displayed in the actual display screen.

Each of the medical support server apparatus 11, the client terminal apparatus 12, and the servers 21 to 23 of the server cluster 13 is composed of a computer (e.g. a server computer, a personal computer, a workstation, or the like) installed with a control program (e.g. an operating system) and an application program (e.g. a server program or a client program).

Figure 5:
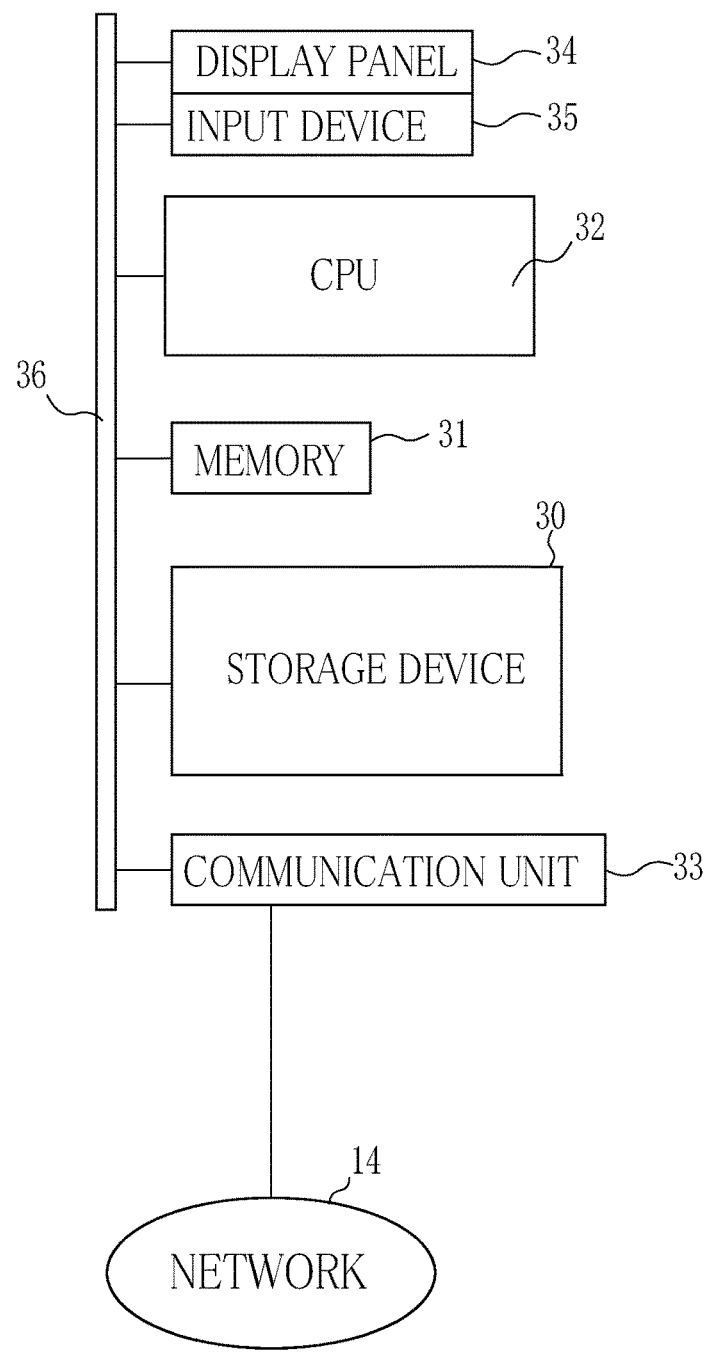
FIG. 5 is a block diagram illustrating a computer that constitutes a medical support server apparatus or a client terminal apparatus.

In FIG. 5, the basic configuration of computers that constitute the medical support server apparatus 11, the client terminal apparatus 12, and the like are the same or substantially the same. Each computer includes a storage device 30, a memory 31, a CPU (Central Processing Unit) 32, a communication unit 33, a display panel 34, and an input device 35, which are interconnected through a data bus 36.

The storage device 30 is incorporated in the computer that constitutes the medical support server apparatus 11, the client terminal apparatus 12, or the like. The storage device 30 may be a hard disk drive connected through a cable or a network. The storage device 30 may be a disk array composed of two or more hard disk drives connected. The storage device 30 stores control programs (e.g. operating systems), various types of application programs, and display data of various types of operation screens associated with the programs.

The memory 31 is a working memory, which is used by the CPU 32 to execute processing. The CPU 32 loads the programs, which are stored in the storage device 30, into the memory 31, and executes the processing in accordance with the program. Thereby, the CPU 32 centrally controls each section of the computer.

The communication unit 33 is a network interface that controls transmissions of various types of information through the network 14. The display panel 34 displays various types of operation screens in accordance with the operation of the input device 35 such as a mouse, a keyboard, or the like. The operation screen is provided with operation functions by a GUI (Graphical User Interface). A computer, which constitutes the medical support server apparatus 11 or the client terminal apparatus 12, receives the input of an operation command from the input device 35 through the operation screen. Incidentally, in the descriptions below, a suffix "A" is attached to a numeral that denotes a part of the computer that constitutes the medical support server apparatus 11, and a suffix "B" is attached to a numeral that denotes a part of the computer that constitutes the client terminal apparatus 12.

Figure 6:
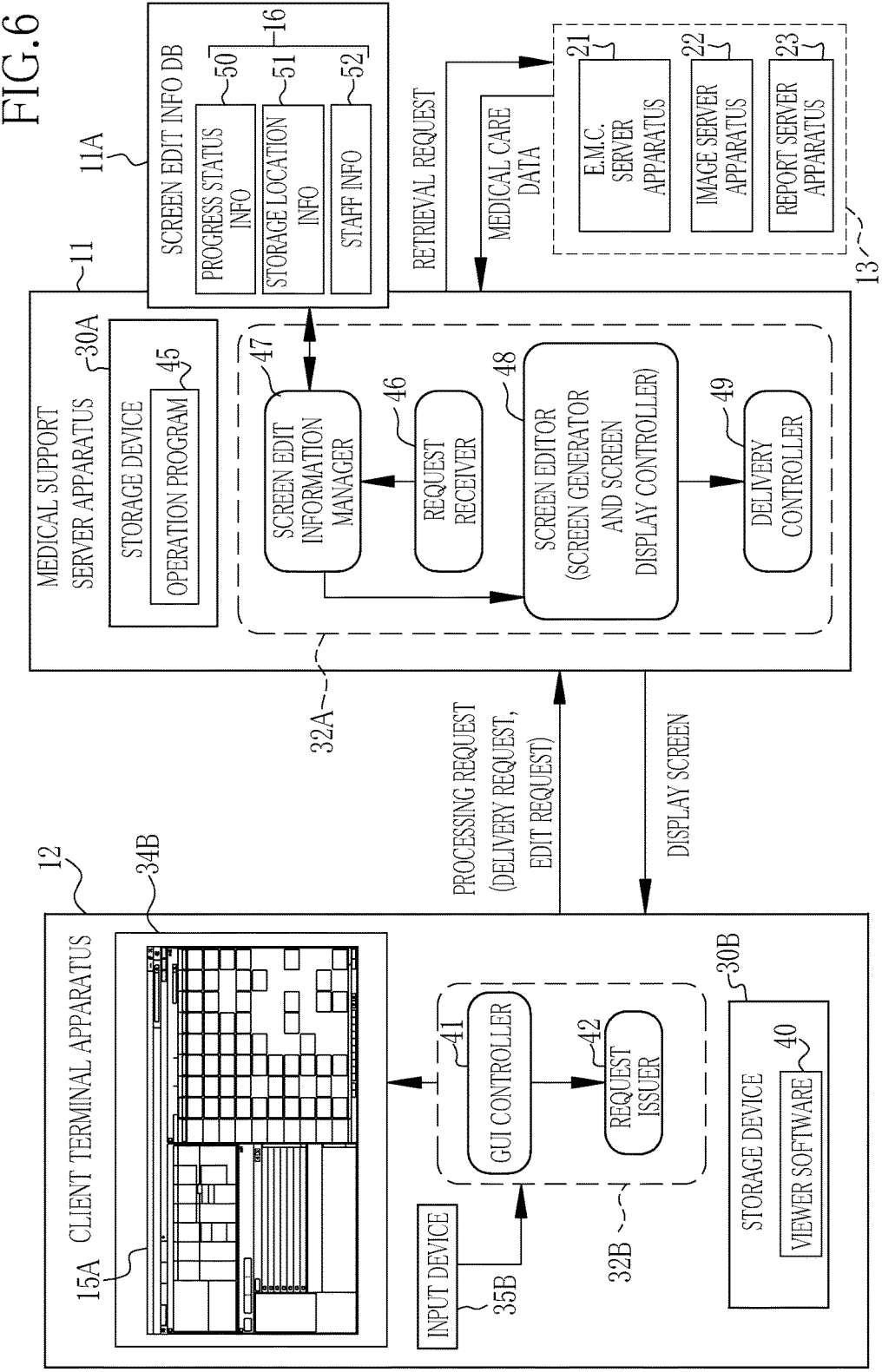
FIG. 6 is a block diagram illustrating each functional part of a CPU of each of the medical support server apparatus and the client terminal apparatus.

In FIG. 6, a storage device 30B of the client terminal apparatus 12 stores viewer software 40 as an application program. The viewer software 40 is used for viewing the first display screen 15A and the second display screen 15B. The viewer software 40 includes two or more gadget engines (hereinafter simply referred to as gadgets) that control the display of multiple display sections that constitute the first display screen 15A and the second display screen 15B. Incidentally, a gadget refers to a subprogram that operates in association with a main application program (e.g. the viewer software 40 or the like) to exert various functions.

Upon the startup of the viewer software 40, a CPU 32B of the client terminal apparatus 12 works together with a memory 31B (not shown in the drawing), thereby functioning as a GUI controller 41 and a command issuer 42.

The GUI controller 41 allows the display of the first display screen 15A or the second display screen 15B, which is delivered from the medical support server apparatus 11, on a web browser of the display panel 34B. The GUI controller 41 controls the output of the screen (the first display screen 15A or the second display screen 15B) in accordance with the operation command inputted from the input device 35B (e.g. clicking a button with use of a cursor 75 (see FIG. 12 or the like)) through the first display screen 15A or the second display screen 15B.

In accordance with (or in response to) the operation command of the input device 35B inputted through the GUI controller 41, the command issuer 42 issues various types of processing commands (processing requests) to the medical support server apparatus 11. The various types of processing commands include a delivery request for the first display screen 15A and edit requests for editing the first display screen 15A and the second display screen 15B. The various types of processing commands, which are issued by the command issuer 42, are transmitted to the medical support server apparatus 11 through the network 14.

The delivery request includes the medical staff ID. The medical staff ID is inputted together with, for example, an authentication key through a log-in screen (not shown in the drawing) for starting up the first display screen 15A.

The edit request requests the medical support server apparatus 11 to edit the display content of the first display screen 15A and the second display screen 15B in accordance with various types of operation commands from the input device 35B. The edit request may include a request designating the patient type. With regard to the types (patient types) of the patients treated in the medical facility having the medical support system 10, there are "patient scheduled for surgery", "outpatient", and "inpatient". The patient scheduled for surgery is a patient who is scheduled to have surgery. The outpatient is a patient who visits the medical facility. The inpatient is a patient who is admitted to the medical facility. Alternatively, for example, the patient type may be determined by the name of his/her disease, such as a patient with gastric cancer. (The "patient scheduled for surgery" is abbreviated as "P.S.S." in the drawing, the same hereinafter.)

An operation program 45 is stored as an application program in the storage device 30A of the medical support server apparatus 11. The operation program 45 is a program that allows the computer constituting the medical support server apparatus 11 to function as the medical support apparatus. Upon the startup of the operation program 45, the CPU 32A of the medical support server apparatus 11 works together with the memory 31A (not shown in the drawing), so that the CPU 32A and the memory 31A function as a command receiver 46, a screen edit information manager 47, a screen editor 48, and a delivery controller 49.

The command receiver 46 receives the delivery request and the edit request from the client terminal apparatus 12. The command receiver 46 outputs the received delivery request and the received edit request to the screen edit information manager 47.

The screen edit information manager 47 manages the screen edit information 16 of the screen edit information DB 11A. The screen edit information 16 is composed of progress status information 50 (see FIG. 7), storage location information 51 (see FIG. 9), and staff information 52 (see FIG. 10). The progress status of a medical care process that the medical staff provides to the patient is stored on a patient-by-patient basis in the progress status information 50. The progress status information 50 is necessary for generating the first display screen 15A. The storage locations of various types of medical care data (e.g. the storage location of the diagnostic image 25 in the image DB 22A, the storage location of the medical report 26 in the report DB 23A, or the like) are stored on a patient-by-patient basis in the storage location information 51. The storage location information 51 is necessary for editing the second display screen 15B. Various types of setting data for the first display screen 15A and the second display screen 15B are stored for each medical staff in the staff information 52.

The screen edit information manager 47 issues a retrieval request for retrieving the medical care data to the server cluster 13 at regular time intervals (for example, at intervals of one hour). The screen edit information manager 47 obtains the medical care data that has been transmitted from the server cluster 13 in response to the retrieval request, and updates the progress status information 50 and the storage location information 51 based on the obtained medical care data. The screen edit information manager 47 updates the staff information 52 in response to the edit request from the command receiver 46. Incidentally, the time intervals for issuing the retrieval request may be changed depending on the type of the medical care data to be retrieved. For example, the retrieval request for the medical care data about the medical examination may be issued at intervals of one hour. The retrieval request for the medical care data other than the medical examination may be issued at intervals of one day.

In response to the delivery request and the edit request from the command receiver 46, the screen edit information manager 47 provides the screen editor 48 with the screen edit information 16 that is necessary for generating or editing the first display screen 15A or editing the second display screen 15B.

The screen editor 48 generates the first display screen 15A based on the screen edit information 16 provided by the screen edit information manager 47. Namely, the screen editor 48 functions as a screen generator.

The screen editor 48 functions as a screen display controller, which controls the display of the first display screen 15A and the second display screen 15B. To be more specific, the screen editor 48 edits the display content of the first display screen 15A and the second display screen 15B based on the edit request received by the command receiver 46. The screen editor 48 changes the display state of a general icon 81C or a small icon 82 (see FIG. 13), in accordance with a change in the progress status of the medical care process performed on the patient by the medical staff.

The delivery controller 49 controls the delivery of the first display screen 15A and the second display screen 15B through a communication unit 33A (not shown in the drawing) to the client terminal apparatus 12 that has transmitted the processing request.

In FIG. 7, the progress status information 50 stores the progress statuses of the medical care processes on a patient ID-by-patient ID basis. The progress status information 50 is composed of items such as the patient type, the medical staff ID of the medical staff in charge (simply referred to as the medical staff ID), the disease name, and the items (medical care process items) of the medical care process. Incidentally, in FIG. 7, the top left tab indicates that the medical staff is a doctor, in other words, the progress status information 50 corresponds to the medical staff type "doctor", by way of example.

One of the "patient scheduled for surgery", the "outpatient", and the "inpatient" is recorded in the item "patient type". The "patient scheduled for surgery" is a patient whose order data in the electronic medical chart 24 has the order for surgery. The "inpatient" is a patient whose treatment record data of the electronic medical chart 24 has the event "hospital admission" but does not yet have the event "hospital discharge". The "inpatient" may be the "patient scheduled for surgery" at the same time. In this case, "the patient scheduled for surgery" is recorded in the item "patient type". The "outpatient" is a patient who is neither the "patient scheduled for surgery" nor the "inpatient". The patient type is determined by referring to the medical care data in the electronic medical chart 24, as described above.

In the item "medical staff ID", the medical staff ID of a medical staff who is in charge of the treatment of the patient is recorded. The medical staff ID recorded in the item "medical staff ID" is the ID of a medical staff of team medicine working in conjunction with each other to treat the patient. The medical staff is determined by the medical staff ID attached to the medical care data.

In the item "disease name", the disease name (e.g. gastric cancer, abbreviated as G.C. in the drawings but fully displayed the actual screen), the date (e.g. "01/23") on which the disease name was recorded, and the medical staff ID (e.g. "D001") of a doctor (attending physician) who recorded the disease name are recorded. The disease name and the medical staff ID are determined by the consultation record data in the electronic medical chart 24. (Note that, as the disease name, in the similar manner as the gastric cancer described above, infiltrating carcinoma is abbreviated as I.C., and appendix is abbreviated as AP. in the drawings, but fully displayed the actual screen.)

The medical care process items include items such as "scheduling of hospitalization" (abbreviated as "S.H." in the drawing, the same hereinafter), "medical examination", "request for anesthesia" (abbreviated as "R.A." in the drawing, the same hereinafter), "preoperative summary" (abbreviated as "PRE.SUM." in the drawing, the same hereinafter), "application for surgery" (abbreviated as "A.S." in the drawing, the same hereinafter), "agreement to anesthesia" (abbreviated as "AG.A." in the drawing, the same hereinafter), "agreement to surgery" (abbreviated as "AG.S." in the drawing, the same hereinafter), and the like. Incidentally, the medical care process items and the like are displayed in abbreviations in terms of space in the drawing but they are fully displayed without abbreviations on the actual screen. The information about each medical care process is recorded in the corresponding item. For example, in the item "scheduling of hospitalization", the date and time on which the scheduling of hospitalization was made (e.g. "01/23 09:30"), the period of scheduled hospitalization (e.g. "01/25 to 01/30"), the hospital room number (e.g. 405), and the type of the room (e.g. single) are recorded. The item "request for anesthesia" displays the date on which the request for anesthesia was made (e.g. "01/23"), the type of anesthesia (e.g. general anesthesia abbreviated as (G) and local anesthesia abbreviated as (L) in the drawing that are fully displayed in the actual screen), and the medical staff ID of the medical staff who received the request for anesthesia (e.g. "D005").

In the examination items, the date of the start of the medical examination (e.g. "01/24") and the progress status of each medical examination are recorded. The various types of medical examinations are displayed in abbreviations. For example, CT examination is abbreviated as "CT", MRI examination is abbreviated as "MR", plain radiography is abbreviated as "DR (Digital Radiography)", ultrasound examination is abbreviated as "US (Ultrasonography)", endoscopic examination is abbreviated as "ES (Endoscopy)", blood test is abbreviated as "BL", biochemical test is abbreviated as "BIO", electrocardiogram is abbreviated as "ECG", electroencephalogram is abbreviated as "EEG", and the like.

The progress statuses of the medical care process items, other than the examinations, include "not-started", "not-completed", and "completed". The progress status "not-started" corresponds to a state in which the medical care process has not been started. The progress status "not-completed" corresponds to a state in which the medical care process has been started but has not been completed. The progress status "completed" corresponds to a state in which the medical care process has been completed. In FIG. 7, the item "agreement to surgery" of the patient ID "0000003210" corresponds to the progress status "not-started". In this case, "not-started" is recorded in the corresponding medical care process item. Each of the items "preoperative summary" and "agreement to anesthesia" of the patient ID "0000003210" corresponds to the progress status "not-completed". In this case, in each medical care process item, the reason why the item has not been completed is described. For example, the preoperative summary has not been completed because it has suspended due to metastasis to liver (denoted as "suspended (A)" in the drawings but the description and the name of the doctor or the like are fully displayed in the actual screen). For example, the agreement to anesthesia has not been completed because the patient's submission of the consent is awaited (denoted as "awaiting" in the drawings but the description and the name of the doctor or the like are fully displayed in the actual screen). In addition, in the medical care process items, the dates on which the reasons are inputted (e.g. "01/20" and the like), and the medical staff IDs of the medical staff who inputted the reasons ("D002" and the like) are also recorded. The progress status "completed" corresponds to the medical care process items such as the preoperative summary of the patient ID "0123456789" and the scheduling of hospitalization of the patient ID "0000254798", for example. The medical care process item corresponding to the unnecessary medical care process (e.g. "agreement to anesthesia" of the patient ID "0000254798") is left blank with nothing recorded in it.

The progress status of the medical examination includes "not-performed", "unconfirmed", and "confirmed". The progress status "not-performed" corresponds to a state in which the medical examination has not been performed. The progress status "unconfirmed" corresponds to a state in which the medical examination has been performed and the medical report 26 has been created but the medical staff has not confirmed the medical report 26. The progress status "confirmed" corresponds to a state in which the medical staff has confirmed the medical report 26. Whether the progress status of the medical examination is "confirmed" or "unconfirmed" depends on whether each medical staff has confirmed the medical report 26. With regard to the medical examinations other than those with the progress status "not-performed" or "confirmed (by all the medical staffs involved in the medical examination)", the medical staff ID of the medical staff who has not confirmed the medical report 26 is displayed along with the medical staff ID of the medical staff who has confirmed the medical report 26 (e.g. "US: D050 with the progress status "unconfirmed" and D001, D005, and D018 with the progress statuses "confirmed" are displayed in the item "examination" of the patient ID "0123456789").

Figure 8:
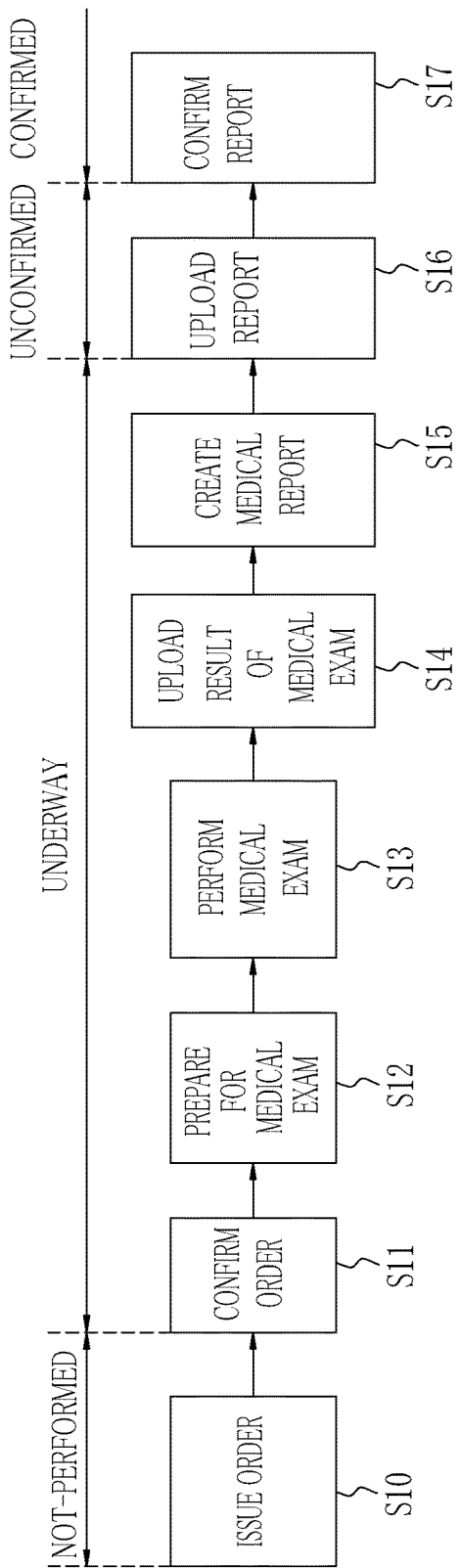
FIG. 8 is an explanatory view illustrating a procedure of a medical examination and each progress status in the procedure.

Here, the medical examination is performed in a procedure illustrated in FIG. 8. First, a doctor of a medical department issues an order for a medical examination on the electronic medical chart 24 (step S10). The issued order is transmitted to the client terminal apparatus 12 of a corresponding examination department, and the laboratory technologist confirms the order through the client terminal apparatus 12 (step S11). Based on the confirmed order, the laboratory technologist makes the examination equipment ready and calls the patient into the examination room to prepare for the medical examination (step S12). Then, the medical examination is performed based on the confirmed order (step S13). After the medical examination, the result of the medical examination is uploaded (step S14). In the case where the medical examination is the imaging examination, the diagnostic image 25 is uploaded as the result of the medical examination to the image DB 22A of the image server apparatus 22. In the case where the medical examination is a laboratory test or a physiological test, the test values are uploaded as the result of the medical examination to the chart DB 21A of the electronic medical chart server apparatus 21. In the case where the medical examination is the imaging examination and the result of the medical examination is uploaded, the radiological doctor in charge of creating the medical report 26 is informed of the upload.

The radiological doctor views the uploaded result of the medical examination through the client terminal apparatus 12, and creates the medical report 26 based on the result of the medical examination (step S15). The medical report 26 is uploaded to the report DB 23A of the report server apparatus 23 (step S16). In the case where the medical report 26 is uploaded, the doctor who ordered the medical examination is informed of the upload.

The doctor views the uploaded medical report 26 through the client terminal apparatus 12, and confirms the content of the medical report 26 (step S17). By referring to the medical report 26, the doctor makes a diagnosis or works out on a treatment plan. The above describes an outline of the procedure of the medical examination.

The progress status "not-performed" corresponds to a period after the order is issued (step S10) and before the order is confirmed (step S11). The progress status "unconfirmed" corresponds to a period after the medical report 26 is uploaded (step S16) and before the medical report 26 is confirmed (step 17). The progress status "confirmed" corresponds to a period after the medical report 26 is confirmed (step S17). Incidentally, the medical examination is underway in a period after the order is confirmed (step S11) and before the medical report 26 is uploaded (step S16). Thus, the progress status of the medical examination changes from moment to moment. The progress status of the medical care process other than the medical examination also changes from moment to moment.

In the storage location information 51 illustrated in FIG. 9, the storage locations of the medical care data are recorded on a patient ID-by-patient ID basis. The storage location information 51 is composed of items such as "diagnostic image 25" and "medical report 26". In addition to the items illustrated, the storage location information 51 includes the items of another medical care data such as "test data", which are the results of the laboratory test or the physiological test, the measurement data of the vital signs, and the like. In each item, a path (for example, "I:¥0123456789¥DR ¥20140808 ¥DR001" or the like) that indicates the storage location of the corresponding medical care data is recorded.

Figure 10:
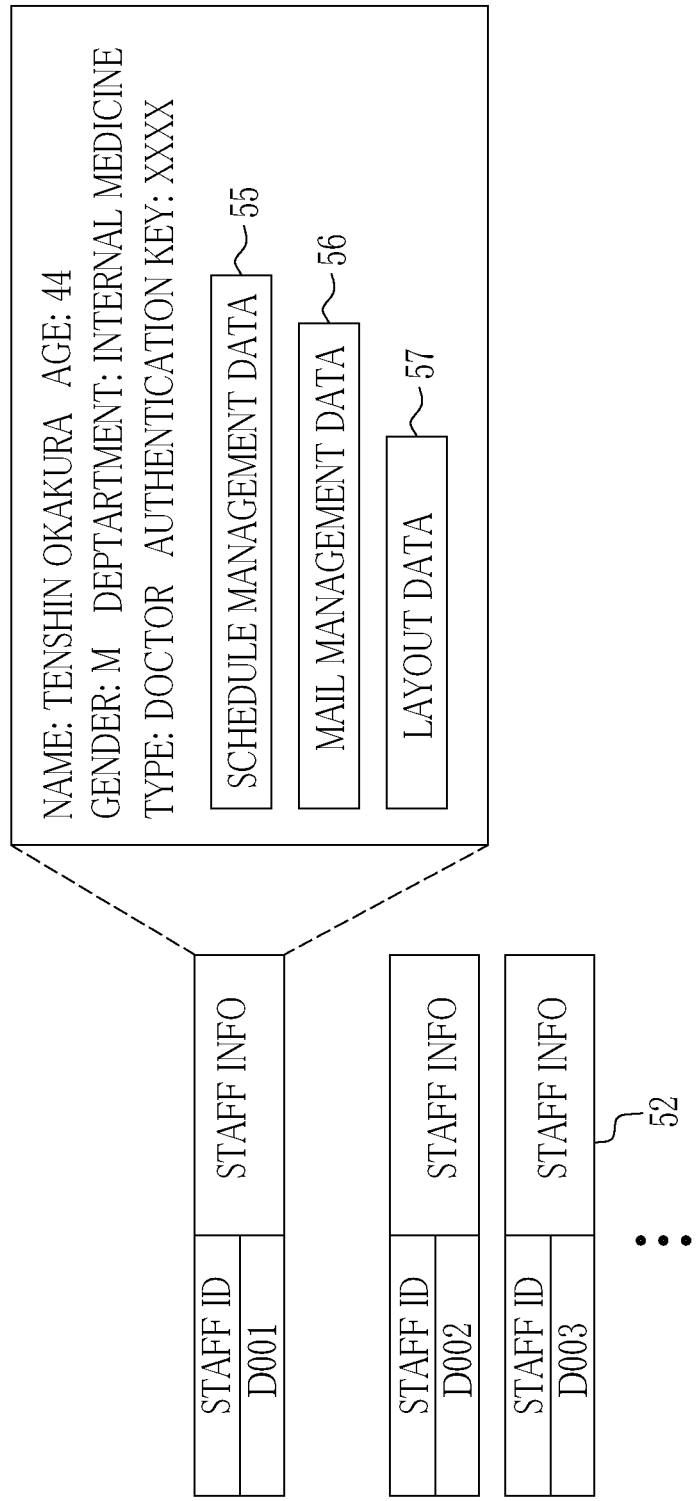
FIG. 10 illustrates the content of staff information.

In FIG. 10, the staff information 52 is associated with the medical staff ID and managed on a medical staff-by-medical staff basis. In the staff information 52, basic information of the medical staff such as the name, age, and gender of the medical staff, the department to which the medical staff belongs, the type of the medical staff (e.g. doctor, laboratory technologist, nurse, or dietician), and the authentication key of the medical staff (the names are displayed in initials in the drawings but the full spellings are displayed in the actual screen, the same hereinafter) are recorded. In addition, in the staff information 52, schedule management data 55, mail management data 56, and layout data 57 are recorded as various types of setting data related to the first display screen 15A and the second display screen 15B.

In the schedule management data 55, the schedule (e.g. outpatient consultation, inpatient rounds, attending a medical congress, class lecture, leave, or the like) of a medical staff is stored in association with the date and time. In the mail management data 56, the e-mails sent to a medical staff and the e-mails written and sent by the medical staff are stored. In the layout data 57, the layout settings of the first display screen 15A and the second display screen 15B which are customized by the medical staff are recorded.

Figure 11:
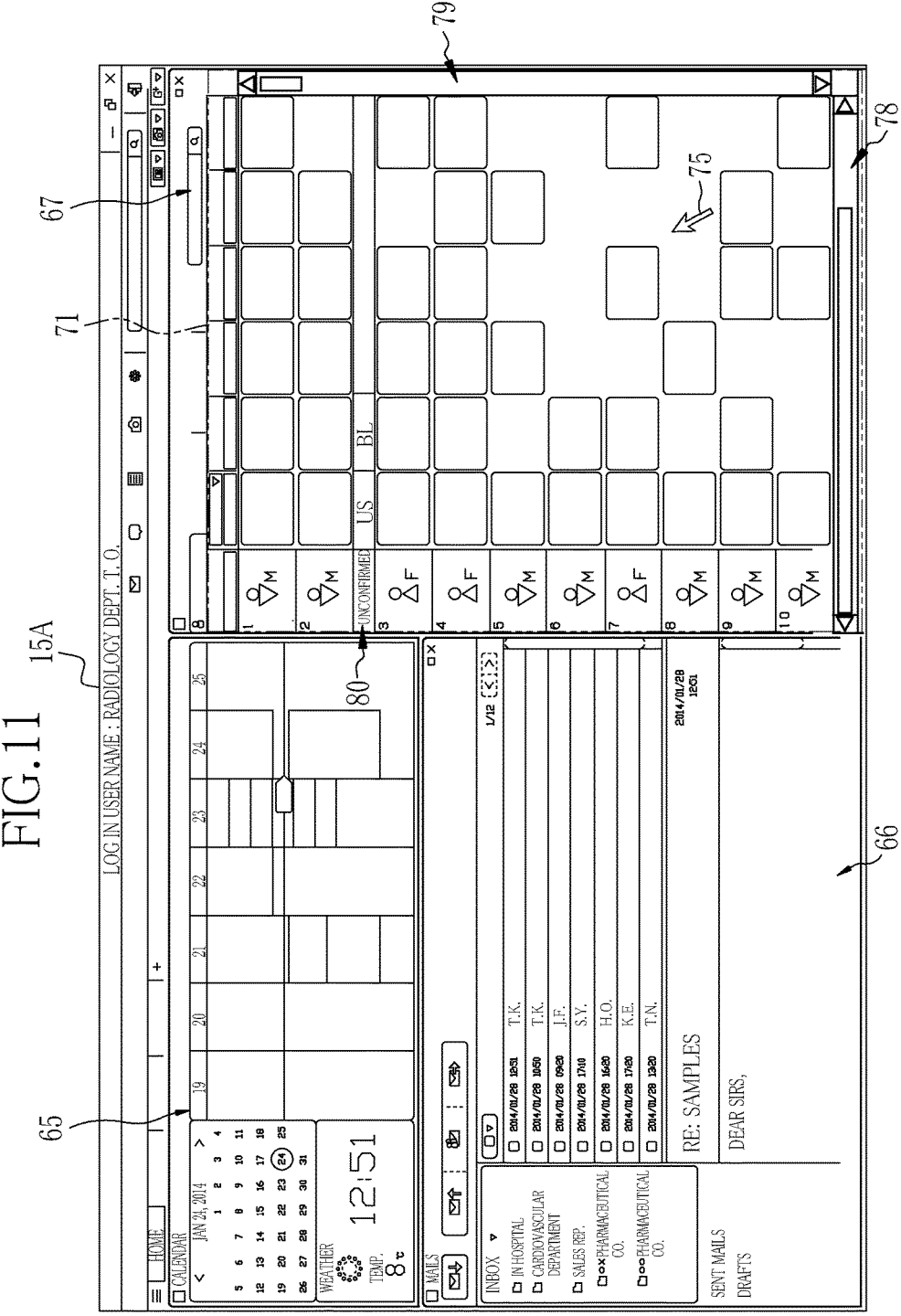
FIG. 11 illustrates a first display screen.

In FIG. 11, the first display screen 15A includes three display sections 65 to 67: the schedule display section 65 in the upper left portion, the mail display section 66 in the lower left portion, and the patient list display section 67 in the right portion.

A schedule management gadget generates the schedule display section 65. The schedule management gadget controls the displays of a calendar, current time, weather of an area in which the medical facility is located, outside-air temperature, and the like in the schedule display section 65. Based on the schedule management data 55, the schedule management gadget also controls the display of weekly schedule of the medical staff whose medical staff ID has been inputted through the log-in screen (the schedule such as the reservations of the medical experiments, the outpatient consultations, and the like is not displayed in the boxes in the calendar in the drawing but it is displayed in the actual screen).

The schedule management gadget accepts a writing operation of the schedule through the schedule display section 65. The command issuer 42 issues the edit request that includes the schedule written through the schedule display section 65. The screen edit information manager 47 records the schedule included in the edit request to the schedule management data 55, and thus updates the schedule management data 55.

The mail display section 66 is generated by the mail management gadget. Based on the mail management data 56, the mail management gadget controls the display of the list of e-mails (those delivered to the medical staff whose medical staff ID has been inputted through the log-in screen) on the mail display section 66 and the display of the content of an e-mail.

The mail management gadget accepts various operations such as confirming for new e-mails, replying the e-mails, and creating e-mails through the mail display section 66. The command issuer 42 issues the edit request that includes various operations inputted through the mail display section 66. The screen edit information manager 47 records the data corresponding to the various operations included in the edit request, on the mail management data 56, and thereby updates the mail management data 56.

The schedule management gadget and the mail management gadget are included in a plurality of gadgets in the viewer software 40. The schedule displayed in the schedule display section 65 and the content of the e-mail displayed in the mail display section 66 are switched in accordance with the medical staff ID inputted through the log-in screen. Incidentally, the positions, areas, and the display contents of the respective display sections 65 to 67 are customized freely by the medical staff. For example, the entire left area may be used as the mail display section 66 and the schedule display section 65 may be dismissed. For example, the schedule display section 65 may be disposed on the lower left and the mail display section 66 may be disposed on the upper left. Such layout settings are recorded in the layout data 57 by the screen edit information manager 47.

A patient list display section 67 displays a patient list 71. The patient list 71 displays the progress statuses of a plurality of medical care processes of the patients treated by a medical staff whose medical staff ID has been inputted through the log-in screen. The progress statuses are displayed on a patient-by-patient basis. Incidentally, each of the patient list display section 67, the schedule display section 65, and the mail display section 66 can be enlarged and displayed full screen in the first display screen 15A.

The patient lists 71 are generated according to the medical staffs by the screen editor 48. To be more specific, for example, in the case where the medical staff ID "D001" is inputted through the log-in screen, the screen edit information manager 47 picks up (retrieves) the progress status information 50 (in FIG. 7, the progress status information 50 of the patient ID "0123456789") in which the medical staff ID "D001" is recorded in the item "medical staff ID", and transmits the retrieved progress status information 50 to the screen editor 48. Based on the progress status information 50 transmitted, the screen editor 48 generates the patient list 71 that represents the progress statuses of the medical care processes of the patients treated by the medical staff having the medical staff ID "D001". Hence, the patients displayed in the patient list 71 vary according the patients who are taken care of by the medical staff.

Figure 12:
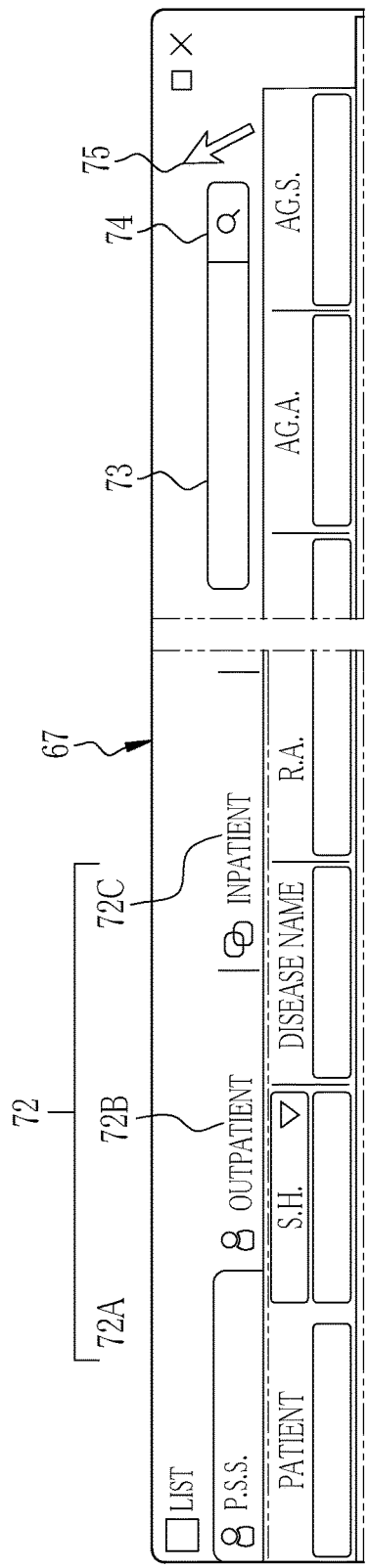
FIG. 12 illustrates an upper part of a patient list display section.

In FIG. 12, a patient type selection tab 72 for selecting (switching) the patient type, a search input box 73 to which the disease name of the patient is inputted as the patient type, and a search button 74 are provided in an upper portion of the patient list display section 67. The patient type selection tab 72 is provided with the tabs 72A, 72B, and 72C representing "patient scheduled for surgery", "outpatient", and "inpatient", respectively. The patient type selection tab 72, the search input box 73, and the search button 74 are provided to narrow down the patients displayed in the patient list 71 by the patient type.

In response to selecting one of the tabs 72A to 72C with use of the cursor 75 from the patient type selection tab 72, or in response to inputting the disease name to the search input box 73 and choosing (clicking) the search button 74 with use of the cursor 75, the command issuer 42 issues the corresponding edit request. The screen edit information manager 47 provides the screen editor 48 with the progress status information 50 that has the patient type, which is designated by the edit request, out of the progress status information 50 picked up (retrieved) based on the delivery request. Based on the progress status information 50 provided by the screen edit information manager 47, the screen editor 48 edits the patient list 71 that is narrowed down by the patient type.

Figure 13:
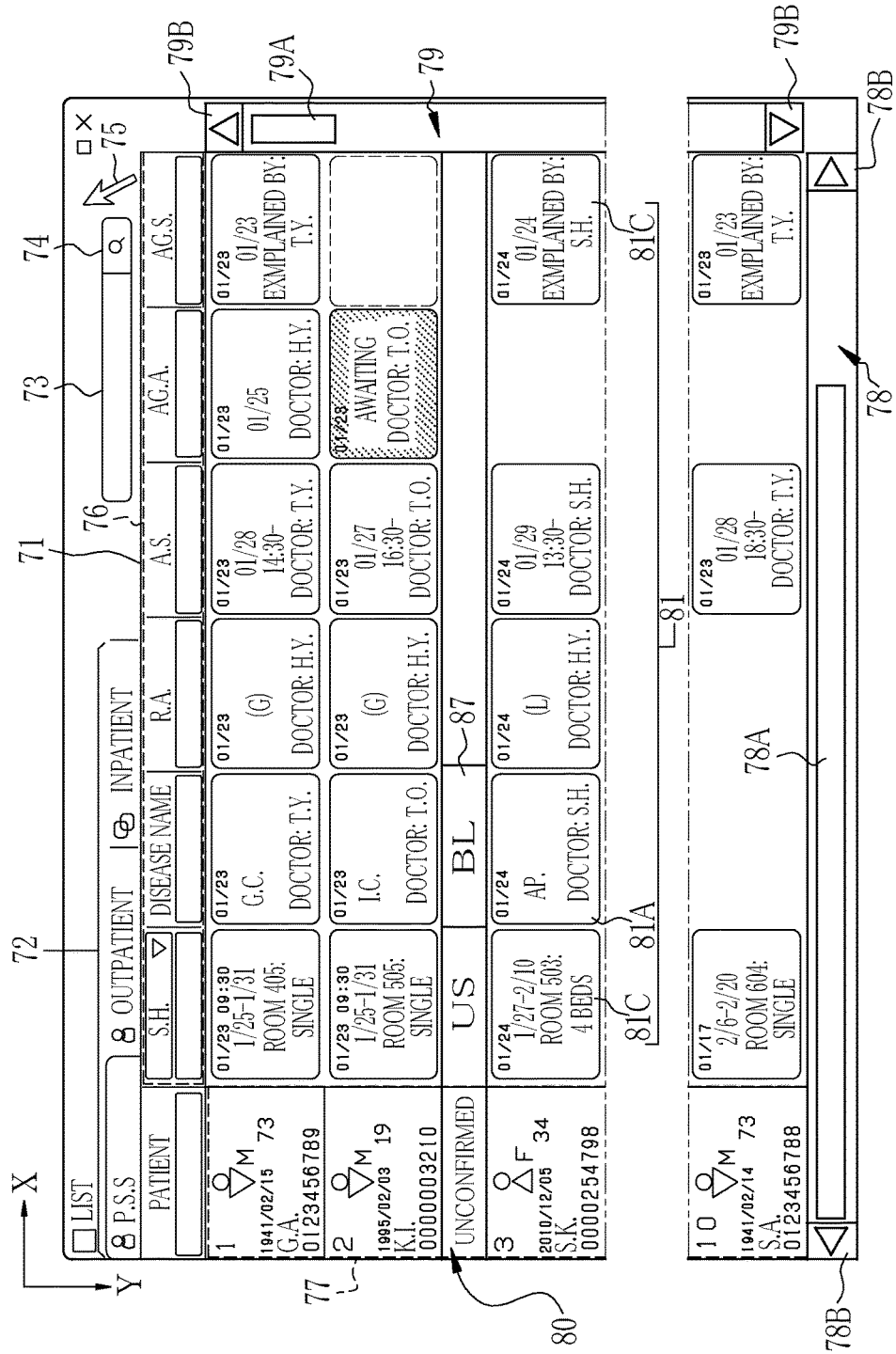
FIG. 13 illustrates the patient list display section.
Figure 14:
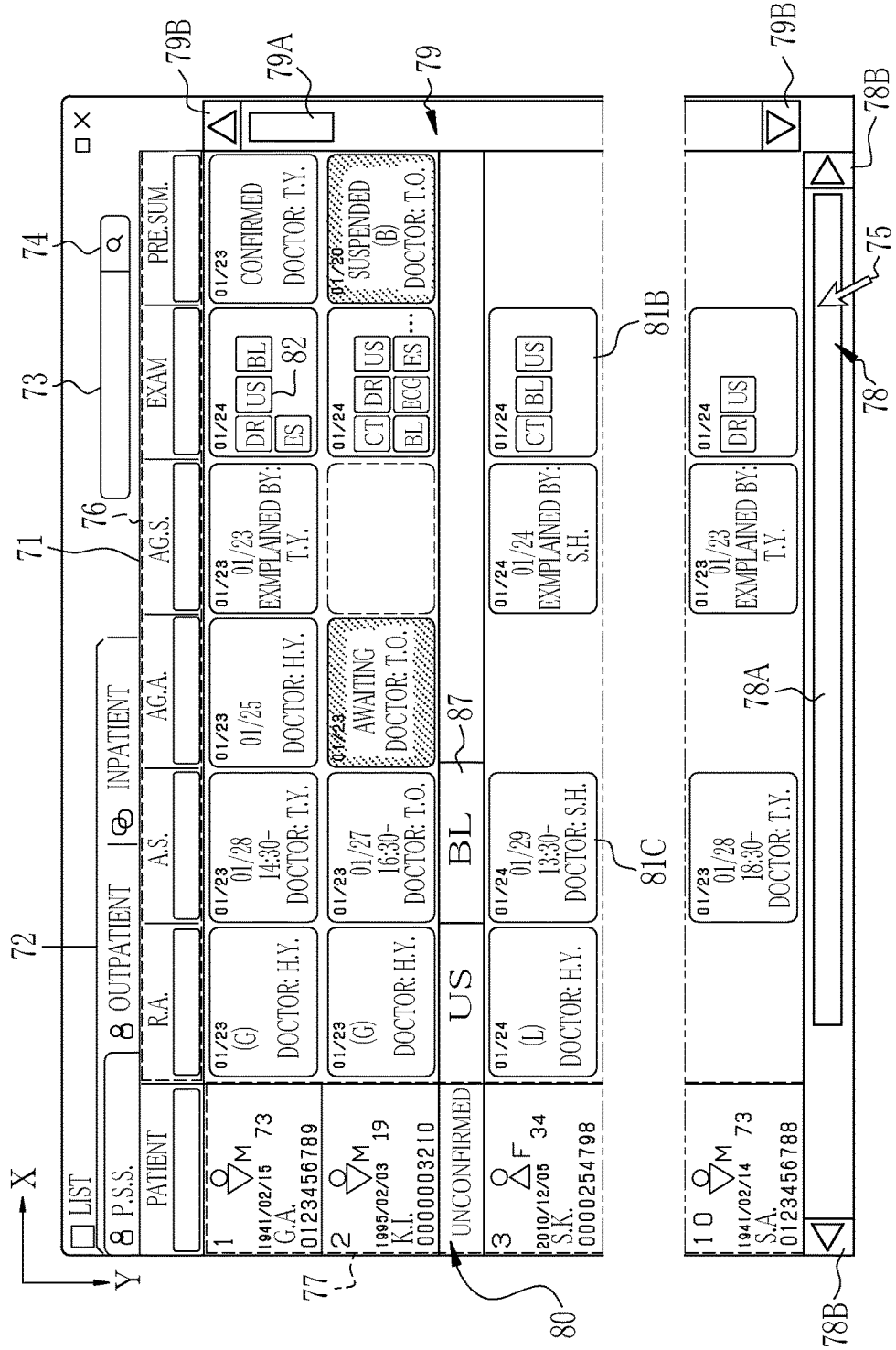
FIG. 14 illustrates the patient list display section in the case where a scrolling operation is performed toward the right from a state illustrated in FIG. 13.

FIGS. 13 and 14 illustrate an example of the patient list 71 corresponding to a case in which the type of the medical staff whose medical staff ID has been inputted through the log-in screen is "doctor" and the tab 72A "patient scheduled for surgery" of the patient type selection tab 72 is selected.

In FIGS. 13 and 14, the patient list 71 includes an item display section 76 and a patient information display section 77. In an upper portion of the patient list 71, the item display section 76 is provided along a horizontal axis X, which corresponds to an item arrangement axis, by way of example. On a left side portion of the patient list 71, the patient information display section 77 is provided along a vertical axis Y, which corresponds to patient identification information arrangement axis, by way of example. The vertical axis Y is orthogonal to the horizontal axis X. In the item display section 76, the medical care process items (illustrated in FIG. 7 by way of example) are arranged. The medical care process items include the items such as the disease name, the scheduling of hospitalization, the request for anesthesia, the application for surgery, the agreement to anesthesia, the agreement to surgery, the examination, and the preoperative summary. The item display section 76 has a sorting function to sort the patients in the patient list 71 to change the order of the patients displayed. For example, the patients may be sorted based on the date of the scheduling of hospitalization or the date of the application for surgery, in an order of earlier to later. Alternatively, the patients may be sorted based on the progress status of a medical care process, in the order of "not-started", "not-completed", and "completed". The patients may be sorted based on the number of the medical examinations with the progress status "not-performed", in descending order.

In the patient information display section 77, the patient information of each patient is displayed along with the number indicating the patient's ordinal position in the list. The patient information refers to the name, the patient ID, gender, the date of birth, and age of the patient described in the electronic medical chart 24. Out of the patient information, the name and the patient ID correspond to patient identification information. The gender is represented by a sign signifying male or female and a letter "M (male)" or "F (female)". For example, the patient information of 10 patients can be displayed at a time in the patient information display section 77 (see FIG. 11).

Icons 81 are arranged in a matrix in a two-dimensional area composed of the item display section 76 and the patient information display section 77. More specifically, the icons 81 are arranged at the intersection points of the items of the item display section 76 and the pieces of the patient information of the patient information display section 77, respectively. There are three types of the icons 81: disease name icons 81A, special icons 81B, and general icons 81C. The icons 81A to 81C are of the same size.

The disease name icon 81A is disposed at the intersection point of the item "disease name" of the item display section 76 and the patient information of the patient information display section 77. In the disease name icon 81A, the disease name, the date on which the disease name was recorded, and the name of the doctor (attending physician) who recorded the disease name are displayed. The disease name and the date on which the disease name was recorded are recorded in the item "disease name" in the progress status information 50. The name of the doctor can be obtained from the staff information 52 of the medical staff ID recorded in the item "disease name" in the progress status information 50. Incidentally, the disease name icon 81A may display the name of the medical department (e.g. neurosurgery or cardiovascular medicine).

The special icon 81B is disposed at the intersection point of the item "examination" of the item display section 76 and the patient information of the patient information display section 77. The special icon 81B displays the date on which the medical examination has started (e.g. "01/24" and the like). The special icon 81B is an icon in which two or more small icons 82 are disposed. For example, six small icons 82 are disposed (or displayed) at the maximum in the special icon 81B.

The small icons 82 represent the progress statuses of the various types of medical examinations, for example, the imaging examinations such as the CT examination, the MRI examination, the plain radiography, the ultrasound examination, and the endoscopic examination, the laboratory tests such as the blood test and the biochemical test, and the physiological tests such as the ECG examination and the EEG examination. The small icon 82 displayed corresponds to only the medical examination whose order has been issued on the electronic medical chart 24 by a doctor in a medical department and that has been scheduled. The small icon 82 is not displayed for the medical examination that is unnecessary and has not been scheduled.

In the small icon 82, letters (or characters) representing the medical examination are displayed. The letters displayed in the small icon 82 are same as the abbreviation of the medical examination described in the item "examination" of the progress status information 50. In other words, the CT examination is abbreviated as "CT", the MRI examination is abbreviated as "MR", the plain radiography is abbreviated as "DR", the ultrasound examination is abbreviated as "US", the endoscopic examination is abbreviated as "ES", the blood test is abbreviated as "BL", the biochemical test is abbreviated as "BIO", the electrocardiogram is abbreviated as "ECG", and the electroencephalogram is abbreviated as "EEG". Since the small icon 82 is smaller in size than the icon 81, simple abbreviation (or initials) with a few letters (e.g. one letter abbreviation, or two- or three-letter abbreviation) is used in the small icon 82 to distinguish the medical examinations from one another.

The general icon 81C is disposed at the intersection point of the medical care process item other than the item "examination" of the item display section 76 and the patient information of the patient information display section 77. In the general icon 81C, text information about the corresponding medical care process is described. The text information is described in legible and understandable letters or characters and is comprehended by viewing the text information. For example, in the general icon 81C disposed in the item "scheduling of hospitalization", the date and time on which the scheduling of hospitalization was made, the period of scheduled hospitalization, the hospital room number, and the type of the room are displayed. In the general icon 81C disposed in the item "request for anesthesia", the date on which the request for anesthesia was made, the type of the anesthesia, and the name of the doctor who accepted (received) the request for anesthesia are displayed. In the general icon 81C disposed in the item "application for surgery", the date on which the application for the surgery was made, the scheduled date and time of the surgery, and the name of the doctor who is scheduled to perform the surgery are displayed. Such information has been recorded in the medical care process items of the progress status information 50. Incidentally, additional text information about the medical care process (e.g. text information about the operative procedure) may be added to the text information in the general icon 81C in the case where an operative procedure of the surgery is to be displayed on the general icon 81C disposed on the item "application for surgery", for example. (Note that, in FIG. 14, the preoperative summary has not been completed because it has suspended due to metastasis to liver, and an anticancer drug is administered. It is denoted as "suspended (B)" in the drawings but the description and the name of the doctor or the like are fully displayed in the actual screen.)

As in the case of the small icon 82, the general icon 81C is displayed only for the medical care process that is scheduled to be performed and whose order (e.g. surgery or the like) is recorded in the order data of the electronic medical chart 24 by a doctor of a medical department. The general icon 81C is not displayed for an unnecessary medical care process (e.g. "agreement to anesthesia" of the patient ID "0000254798"). Such unnecessary medical care process in the patient list 71 is left as a blank space 83 (see FIG. 18).

The icons 81A to 81C are displayed in predetermined colors, respectively, on an item-by-item basis. For example, the color of the general icon 81C disposed at the item "scheduling of hospitalization" is russet brown. The color of the special icon 81B and the small icon 82 disposed at the item "examination" is yellow ocher (ochre). The color of the general icon 81C disposed at the item "request for anesthesia" is greenish brown. The color of the general icon 81C disposed at the item "application for surgery" is dark green. The color of the general icon 81C disposed at the item "agreement to surgery" is indigo blue. The icons 81A to 81C are displayed in chromatic colors. Normally, the letters and characters in each of the icons 81A to 81C and the small icons 82 and the frames (frame lines) of the small icons 82 are displayed in white (in other words, white characters and white frame lines are on a colored background), for example.

The patient list 71 includes a horizontal scroll bar 78 and a vertical scroll bar 79 (also see FIG. 11). The horizontal scroll bar 78 is disposed along the horizontal axis X in a lower portion of the patient list 71, namely, on the opposite side of the item display section 76. The vertical scroll bar 79 is disposed along the vertical axis Y at the right side of the patient list 71, namely, on the opposite side of the patient information display section 77. The scroll bars 78 and 79 have the same structure. The scroll bar 78 has a slider 78A movable in the scroll bar 78, and a pair of arrow buttons 78B disposed at both ends of the scroll bar 78. The scroll bar 79 has a slider 79A movable in the scroll bar 79, and a pair of arrow buttons 79B disposed at both ends of the scroll bar 79.

The screen editor 48 provides the horizontal scroll bar 78 in the patient list 71 in the case where a part of a plurality of the items and the icons 81 disposed at the part of the items are not contained within the first display screen 15A and hidden (i.e., become hidden sections) due to the setting of the layout of the first display screen 15A based on the layout data 57 or the like. Further, the screen editor 48 provides the vertical scroll bar 79 in the patient list 71 in the case where a part of a plurality of pieces of the patient information (patient identification information) are not contained within the first display screen 15A and hidden.

In FIG. 13, the item "examination" and the item "preoperative summary" are hidden among the items "scheduling of hospitalization", "request for anesthesia", "application for surgery", "agreement to anesthesia", "agreement to surgery", "examination", and "preoperative summary". Further, the patient information of 10 patients are displayed in ascending order from first to tenth, and the patient information of other patients are hidden.

The screen editor 48 displays an unconfirmed medical-care-process display section 80 on the first display screen 15A in a state that the horizontal scroll bar 78 and the vertical scroll bar 79 are provided in the patient list 71 (also see FIG. 11). The unconfirmed medical-care-process display section 80 is a display section for representing that there is an unconfirmed medical care process which has not been confirmed in the case where the result of the medical care process whose progress status is represented by the icon 81 that is hidden has not been confirmed by a medical staff.

In FIG. 13, the icons 81 that are hidden correspond to the special icon 81B disposed at the item "examination" and the general icon 81C disposed at the item "preoperative summary". The result of the medical care process whose progress status is represented by the icon 81 that is hidden corresponds to the medical report 26 as the reporting of the result of each medical examination whose progress status is represented by the small icon 82 of the special icon 81B. The unconfirmed medical care process is the medical examination whose progress status is "unconfirmed". Incidentally, the preoperative summary is not specifically required to be confirmed by the medical staff (i.e., the preoperative summary is not the medical care process required to be confirmed). Therefore, although being hidden, the preoperative summary is not a target to be displayed in the unconfirmed medical-care-process display section 80. Only the medical examination which is the medical care process required to be confirmed is the target to be displayed in the unconfirmed medical-care-process display section 80.

The unconfirmed medical-care-process display section 80 is inserted between the icons 81 of the patients arranged along the horizontal axis X, and displayed. In FIG. 13, the unconfirmed medical-care-process display section 80 of the second patient having the patient ID "0000003210" in ascending order is inserted between the icons 81 of the second patient having the patient ID "0000003210" and the icons 81 of the third patient having the patient ID "0000254798" in ascending order, and displayed.

The unconfirmed medical-care-process display section 80 is constituted by arranging blocks 87 each corresponding to the icon representing the progress status of the unconfirmed medical care process in the horizontal axis X direction. In FIG. 13, the icons representing the progress statuses of the unconfirmed medical care process correspond to the small icons 82 representing the progress statuses of various types of medical examinations. The width of the block 87 in the horizontal axis X direction is approximately equal to that of the icon 81, and the height of the block 87 in the vertical axis Y direction is approximately half of that of the icon 81.

As in the case of the small icon 82, the letters or characters representing various types of the medical examinations are displayed in the block 87. In FIG. 13, two blocks 87 are exemplified. "US" representing the ultrasonography is displayed on one of the two blocks 87, and "BL" representing the blood test is displayed on the other of the two blocks 87.

The block 87 on which the "US" is displayed is disposed at the column of the item "scheduling of hospitalization" as the head item in the patient list 71. The block 87 on which "BL" is displayed is disposed at the column "disease name" as the second item in the patient list 71, next to the item "scheduling of hospitalization". As described above, the blocks 87 are aligned and displayed at the head position of the items at the side of the patient information display section 77 in which a plurality of pieces of the patient information are arranged.

The hidden section is allowed to be displayed by a scrolling operation such as operation of the slider 78A or 79A and the arrow button 78B or 79B with use of the cursor 75, or rotation of a wheel button of the mouse. For example, as shown in FIG. 14, in the case where the scrolling operation is performed to the right, the item "examination" and the item "preoperative summary" that are hidden and the icons 81 disposed at the hidden items in FIG. 13 are displayed on the first display screen 15A. Instead, in FIG. 14, the item "scheduling of hospitalization", the item "disease name", and the icons 81 disposed at each of the items, which are shown in FIG. 13, are hidden. Incidentally, even if the scrolling operation is performed, the position at which each of the item display section 76, the patient information display section 77, and the unconfirmed medical-care-process display section 80 is displayed is fixed.

The medical care process performed on the patient by the medical staff varies depending on the patient type and the medical staff type. For example, in the case where the patient type is the "outpatient", the medical care processes related to the hospital admission or the surgery (e.g. the scheduling of hospitalization and the application for surgery illustrated in FIG. 13) are unnecessary. In the case where the medical staff type is the "dietician", the medical care processes that are not illustrated in FIG. 13 (e.g. creation of hospital meal plans for the inpatients and dietary instructions to the inpatients) are necessary. Thus, the items displayed in the item display section 76 of the patient list 71 vary depending on the patient type and the medical staff type as illustrated in an item list 84 organized according to patient types and medical staff types in FIG. 15.

In FIG. 15, for example, in the case where the patient type is the "patient scheduled for surgery" and the medical staff type is the "doctor", the items displayed in the item display section 76 are the "disease name", the "scheduling of hospitalization", the "examination", the "request for anesthesia", the "preoperative summary", the "application for surgery", the "agreement to anesthesia", the "agreement to surgery", and the like shown in FIG. 13. For example, in the case where the patient type is "outpatient", the items such as "disease name", "examination", and "patient referral" are displayed regardless of the medical staff type. The "patient referral" is a document that describes the medical care information (medical care data) about the outpatient who was referred by a doctor of another medical facility.

For example, in the case where the patient type is the "inpatient" and the medical staff type is the "doctor", the items such as "disease name", "meal", "scheduling of hospitalization", "examination", "application for surgery", "clinical path", "pressure ulcer management plan", "nutritional management plan", "therapeutic plan following hospital discharge", and "hospital discharge summary" are displayed.

The clinical path is created by a doctor and describes the disease name of the inpatient, the symptoms thereof, a therapeutic plan, examinations, the content of the surgery and the scheduled date of the surgery, and the estimated period of hospitalization. The pressure ulcer management plan is created by a nurse and describes information about prevention and treatment of pressure ulcer (the so-called bedsore) due to a long-term hospital admission. The nutritional management plan is created by a dietician and describes information about hospital meals such as creation of hospital meal plans for the inpatients and nutrition education for the inpatients. The therapeutic plan following hospital discharge is created by a doctor and describes the estimated date of the hospital discharge, the condition of the patient at the time of the hospital discharge, the treatment plan following the hospital discharge, precautions in daily life (e.g. rest levels, meals, taking medicine, and taking a bath), and guides to health and welfare services. The hospital discharge summary is a summary of the results of the medical examinations performed during the hospital admission.

As described above, the items displayed in the item display section 76 vary depending on the medical staff type. Therefore, in addition to the progress status information 50 for doctors (see FIG. 7), the progress status information 50 for other medical staff such as nurses or dieticians is stored. The patient list 71 in accordance with the patient type and the medical staff type is generated and edited by the screen editor 48. An example of the patient list 71 in FIG. 16 shows that the medical staff type whose medical staff ID has been inputted through the log-in screen is the "dietician" and a tab 72C (the inpatient) of the patient type selection tab 72 has been chosen.

Figure 16:
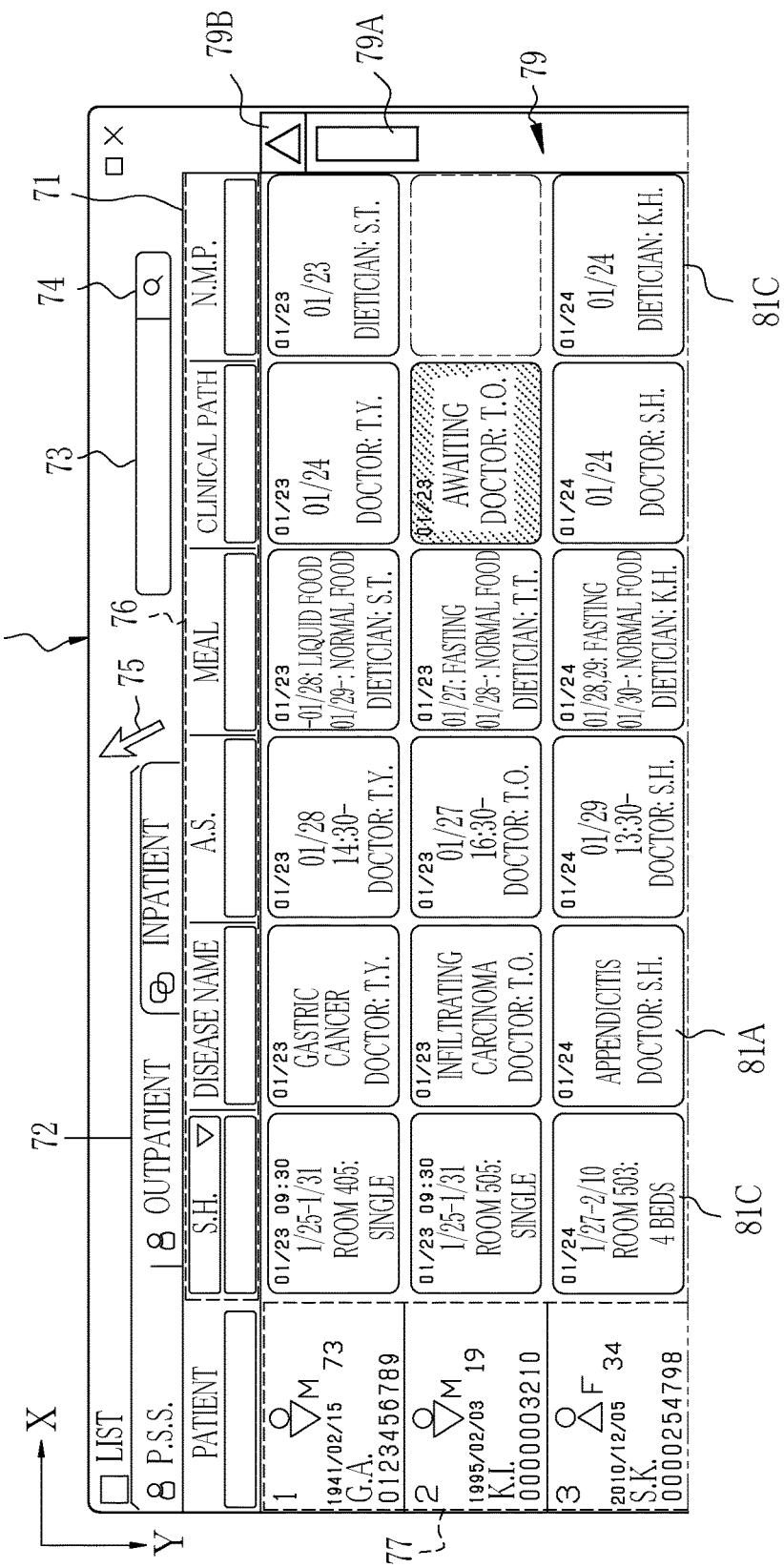
FIG. 16 illustrates a patient list in the case where the patient type is "inpatient" and the medical staff type is "dietician"

The item display section 76 of the patient list 71 illustrated in FIG. 16 displays each of the items (disease name, meal, scheduling of hospitalization, examination, application for surgery, clinical path, nutritional management, and therapeutic plan following hospital discharge) described in the item corresponding to the patient type "inpatient" and the medical staff type "dietician" in the item list 84 organized according to patient types and medical staff types shown in FIG. 15. In FIG. 16, the items "disease name", "meal", "scheduling of hospitalization", "application for surgery, "clinical path", and "nutritional management plan" are displayed (i.e., correspond to the display sections), and the items "examination" and "therapeutic plan following discharge" are hidden (i.e., correspond to hidden sections).

The icons 81 are arranged at a matrix on the intersection points of the above-described items and the patient information, respectively, in a manner similar to those shown in FIG. 13. The general icon 81C arranged in the column corresponding to the item "meal" displays the dates before and after the surgery, the types of meals (e.g. liquid diet, fasting, or normal meal), and the name of the dietician in charge. Each of the normal icons 81C disposed at the items "clinical path", "nutritional management", and "therapeutic plan following hospital discharge" displays the date each of the documents was submitted and the name of the medical staff who created each of the documents. (The normal icons 81C disposed at the item "therapeutic plan following hospital discharge" is hidden, and therefore not shown in the drawing.)

Incidentally, in the case where the patient type is "outpatient", the general icon 81C disposed at the item "patient referral" displays the name of the medical facility from which the patient was referred, the name of the doctor who referred the patient, and the like in text form (text information) (not shown in the drawing). The items are not limited to those described above. For example, items such as "request for blood transfusion", "agreement to blood transfusion", or the like may be added in the case where the surgery needs blood transfusion. An item "application for ICU (Intensive care unit)" may be added in the case where a patient uses ICU. For example, items of daily medical care processes for the inpatients (e.g. thermometry, pulse measurement, blood pressure measurement, blood collection) may be added for the medical staff type "nurse". The items of examinations may be changed according to the medical staff types. In the case where the medical staff type is "doctor", "nurse", or "laboratory technologist", all the medical examinations including the imaging examination, the laboratory test, and the physiological test may be displayed as the examination items. In the case where the medical staff type is "dietician", only the laboratory test may be displayed as the examination item.

Figure 17:
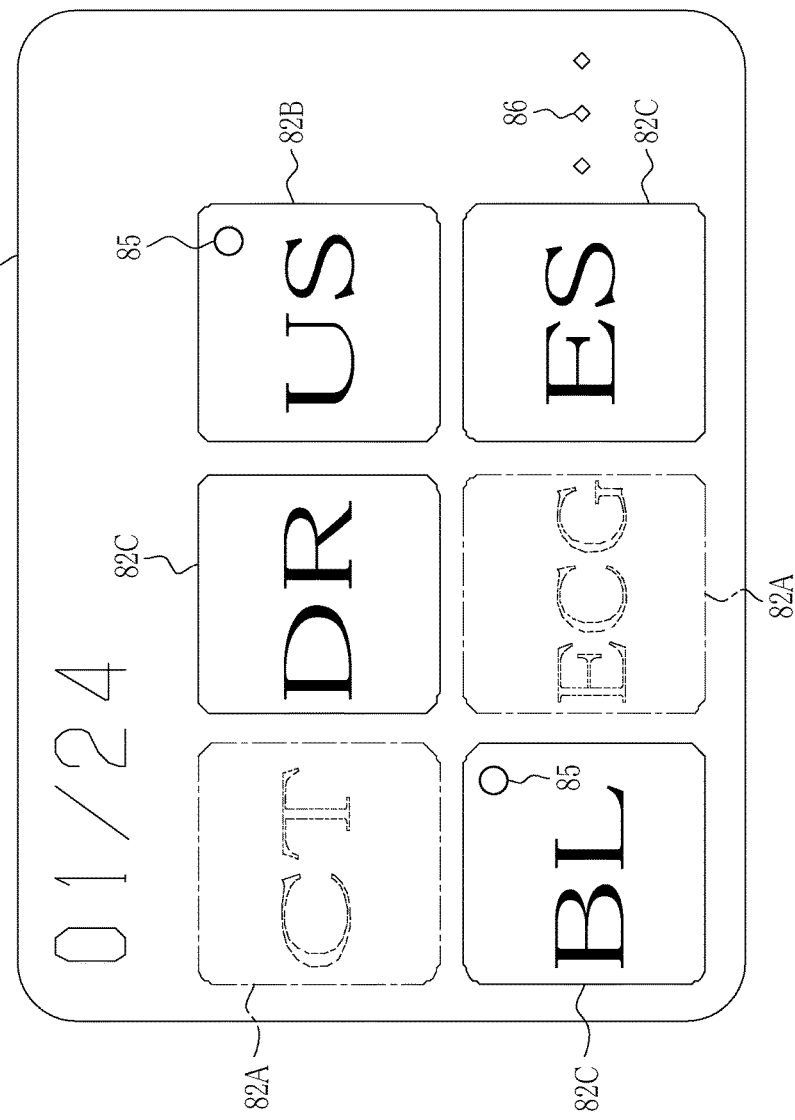
FIG. 17 illustrates an example of progress status displayed, the progress status being represented by small icons.

As illustrated in FIG. 17, the screen editor 48 varies the display state of the small icon 82 in accordance with a change in the progress status of the corresponding medical examination. To be more specific, for example, in the case where the progress status is "not-performed", the letters (or characters) and the frame lines of the small icons 82A (for example, "CT" and "ECG") depicted by chain and dot lines are displayed in an achromatic color (e.g. gray). In the case where the progress status is "unconfirmed", for example, as in the case of the small icons 82B that represent "US" and "BL", the letters and the frame lines are displayed in white color and an "unconfirmed" mark 85 is displayed in the small icon 82B. In the case where the progress status is "confirmed", for example, as in the case of the small icons 82C that represent "DR" and "ES", the letters and the frame lines are displayed in white. The two blocks 87 of the unconfirmed medical-care-process display section 80, on one of which "US" is displayed, and on the other of which "BL" is displayed, as shown in FIG. 13, correspond to the two small icons 82B of "US" and "BL" in each of which the "unconfirmed" mark 85 is displayed, as shown in FIG. 17.

As illustrated in FIG. 7, whether the progress status of the medical examination is "confirmed" or "unconfirmed" depends on the medical staff in charge. For example, in the case where the medical staff ID which has been inputted through the log-in screen is "D007", "US, BL: D007 unconfirmed" has been recorded in the item "examination" of the patient having the patient ID "0000003210" in the progress status information 50. Therefore, the "unconfirmed" mark 85 is displayed in the small icons 82 that represent "US" and "BL", as in the case of the small icons 82b shown in FIG. 17. In the case where the medical staff ID which has been inputted through the log-in screen is "D002", "US, BL: D002 confirmed" has been recorded in the item "examination" of the patient having the patient ID "0000003210" in the progress status information 50. Therefore, the "unconfirmed" mark 85 is not displayed in the small icons 82 that represent "US" and "BL", and the small icons 82 that represent "US" and "BL" are displayed in the same manner as the small icons 82C representing "DR" and "ES". Thus, the progress statuses displayed on the patient list 71 vary according to the medical staffs.

Incidentally, the reference numeral 86 denotes an "and so on" mark, which is displayed in the case where there are more than six types of medical examinations, in other words, in the case where the number of the small icons 82 is greater than six, which is the maximum number of the small icons 82 displayed at a time in the special icon 81B. In response to choosing of the "and so on" mark 86 with use of the cursor 75, the small icons 82 that have not appeared in the special icon 81B are displayed in a pop-up box (window) over the special icon 81B.

Figure 18:
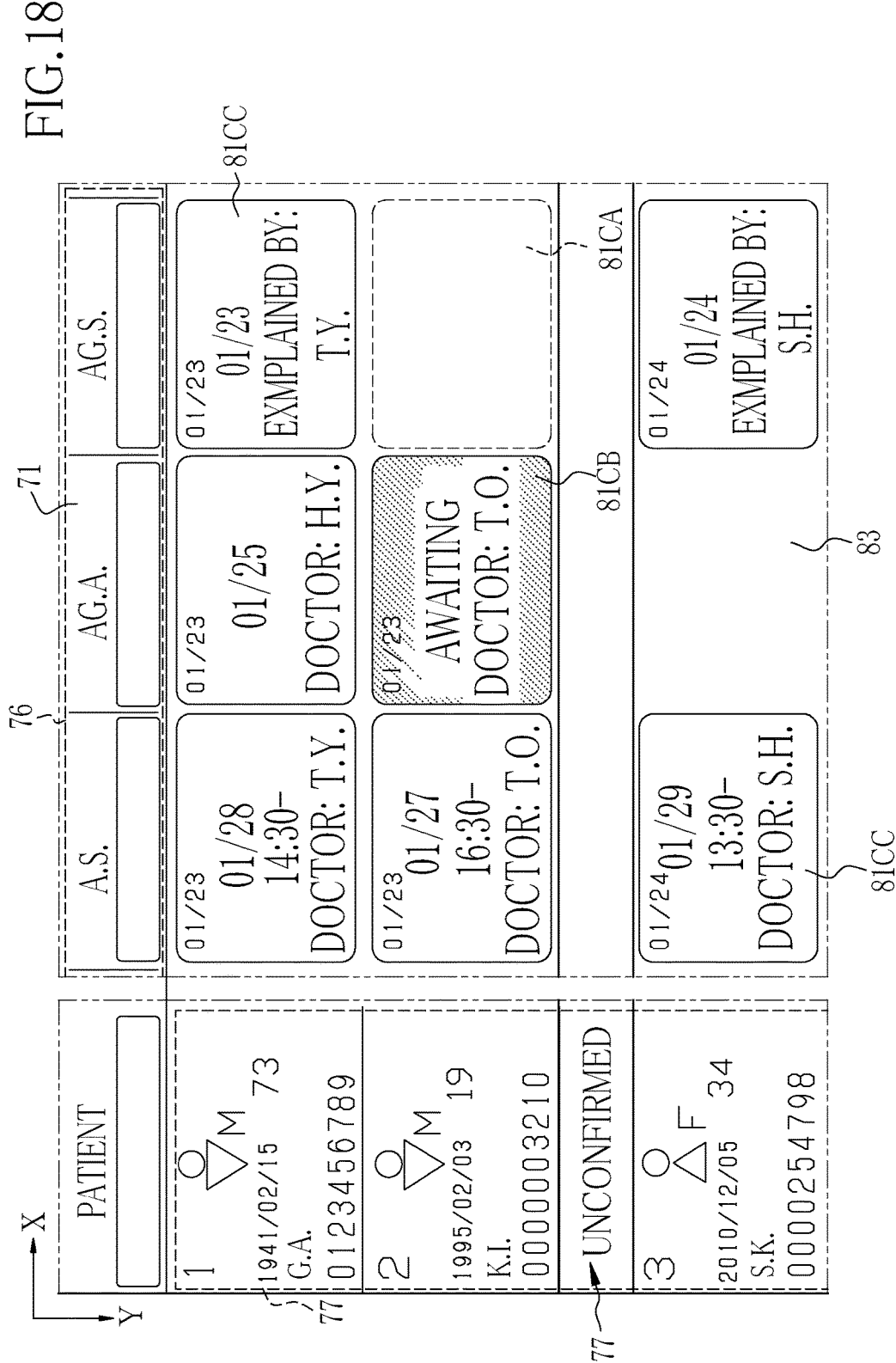
FIG. 18 illustrates an example of progress status displayed, the progress status being represented by general icons.

As illustrated in FIG. 18, the screen editor 48 changes the display state of the general icon 81C in accordance with a change in the progress status of the medical care process other than the medical examination. To be more specific, in the case where the progress status is "not-started", the icon is displayed not in the chromatic color set for the icon but in an achromatic color (in this example, white) and the frame lines of the icon are depicted with dotted lines (see, for example, the general icon 81CA depicted with the dotted lines and located at the intersection point of the item "agreement to surgery" and the patient ID "0000003210"). In the case where the progress status is "not-completed", the icon is displayed not in the chromatic color set for the icon but in an achromatic color (in this example, gray) and the letters (or characters) in the icon are displayed in white (see, for example, the general icon 81CB with hatch lines located at the intersection point of the item "agreement to anesthesia" and the patient ID "0000003210". In the case where the progress status is "completed", the icon is displayed in the chromatic color set for the icon and the letters in the icon are displayed in white (see, for example, the general icons 81CC corresponding to the patient ID "0123456789" and the general icon 81CC located at the intersection point of the item "application for surgery" and the patient ID "0000003210".

In the case where the patients are narrowed down by the patient type, the patient information display section 77 of the patient list 71 displays only the patient information of the patients narrowed down by the patient type. The general icon 81C and the small icon 82 display the progress statuses of the medical care processes corresponding to the patients narrowed down by the patient type. Thus, the patients displayed on the patient list 71 and the progress statuses vary according to the patient types. Incidentally, before narrowing down the patients by the patient type, the patients of the types "patient scheduled for surgery", "outpatient", and "inpatient" are mixed in the patient list 71 generated.

Each piece of the patient information in the patient information display section 77 is selectable with use of the cursor 75. In the case where the patient information is selected with use of the cursor 75, the command issuer 42 issues an edit request for editing the second display screen 15B in which the results of the medical examination and the medical report 26 of the patient whose patient information has been selected with use of the cursor 75 are to be displayed. The screen edit information manager 47 picks up (retrieves) the storage locations of various types of medical care data corresponding to the patient ID of the patient whose patient information has been selected with use of the cursor 75, from the storage location information 51. The screen edit information manager 47 accesses the storage locations which has been picked up, and retrieves the medical care data necessary for generating the second display screen 15B, and transmits the retrieved medical care data to the screen editor 48. Based on the medical care data transmitted from the screen edit information manager 47, the screen editor 48 edits the second display screen 15B.

Figure 19:
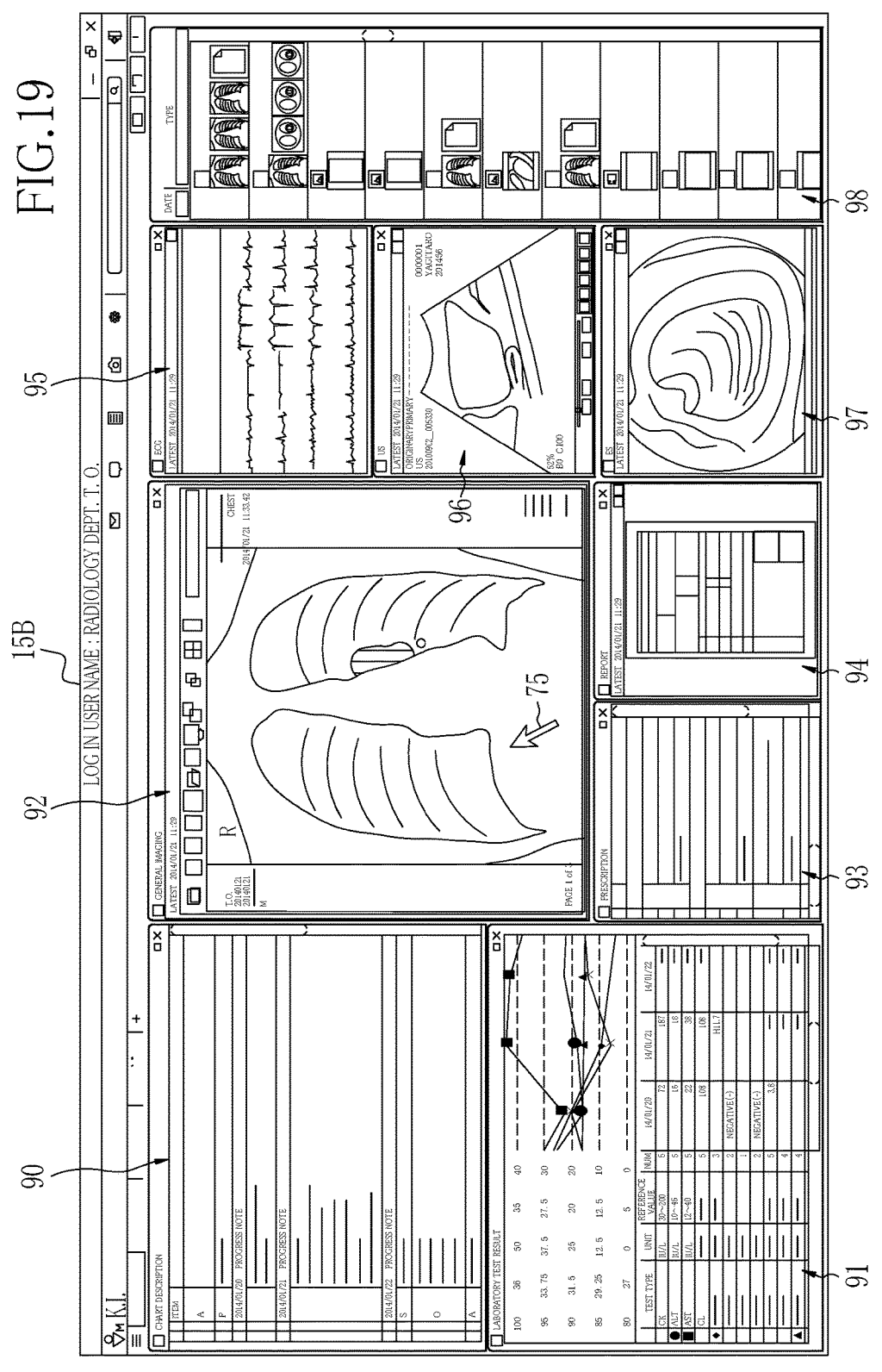

In FIG. 19, the second display screen 15B includes nine display sections 90 to 98: a chart description display section 90 located in an upper left portion, a laboratory test result display section 91 located in a lower left portion, a DR (digital radiography or plain radiography) result display section 92 located in an upper center portion, a prescription display section 93 and a report display section 94 located in a lower center portion, an ECG (electrocardiogram) result display section 95 located in an upper right portion, a US (ultrasound) result display section 96 located in a right center portion, an ES (endoscopy) result display section 97 located in a lower right portion, and an examination history display section 98 located in a right end portion. The second display screen 15B is a display screen that displays the results of various types of medical examinations and the medical reports 26 as detailed information of the medical care processes.

The second display screen 15B is displayed, in place of the first display screen 15A, on the display panel 34B of the client terminal apparatus 12, while the display of the first or second display screen 15A or 15B is selectable. Alternatively, the first and second display screens 15A and 15B may be displayed independently on the display panel 34B.

The display position, the area, and the display content of each of the display sections 90 to 98 in the second display screen 15B is customized freely by the medical staff, and the layout settings are recorded in the layout data 57, in a manner similar to those of the display sections 65 to 67 in the first display screen 15A. For example, the display sections for the results of other medical examinations (e.g. a CT examination result display section or an MRI examination result display section) or a display section for displaying the agreement to anesthesia, the agreement to surgery, or the like may be added.

In the chart description display section 90, a chart description display gadget chronologically displays the descriptions (e.g. consultation record data and the like in the electronic medical chart 24) (the descriptions are not displayed in FIG. 19 but they are displayed in the actual screen). In the laboratory test result display section 91, a laboratory test result display gadget chronologically displays the test values as the test results (e.g. the blood test values, the biochemical test values, and the like) and graph(s) indicating changes in test values with time (the dates, the types of tests, the reference values and the measurement values of each test are not displayed in FIG. 19 but they are displayed chronologically in the actual screen). In the DR result display section 92, the DR result display gadget displays an X-ray image captured in the DR examination. In the prescription display section 93, a prescription display gadget chronologically displays the prescriptions of the medication based on the order data of the medication and the treatment record data in the electronic medical chart 24 (the date and the details of the prescriptions are not displayed in FIG. 19 but they are displayed in the actual screen).

In the report display section 94, a report display gadget displays the medical report 26. In the ECG result display section 95, an ECG result display gadget displays an ECG image captured in the ECG examination (the date and time and the like are not displayed in FIG. 19 but they are displayed in the actual screen). In the US result display section 96, a US result display gadget displays an ultrasonic image captured in the US examination (the date and time and the like are not displayed in FIG. 19 but they are displayed in the actual screen). In the ES result display section 97, an ES result display gadget displays an endoscopic image captured in the ES examination (the date and time and the like are not displayed in FIG. 19 but they are displayed in the actual screen). In the examination history display section 98, an examination record display gadget chronologically displays the histories of various types of medical examinations that the patient had (the types of the medical examinations and the like are not displayed in FIG. 19 but they are displayed in the actual screen and the examination history display section 98 is enlarged and displayed in FIG. 20). The above-described gadgets are part of the gadgets included in the viewer software 40. Incidentally, each of the display sections 90 to 98 may be enlarged and displayed to cover the entire second display screen 15B.

Figure 20:
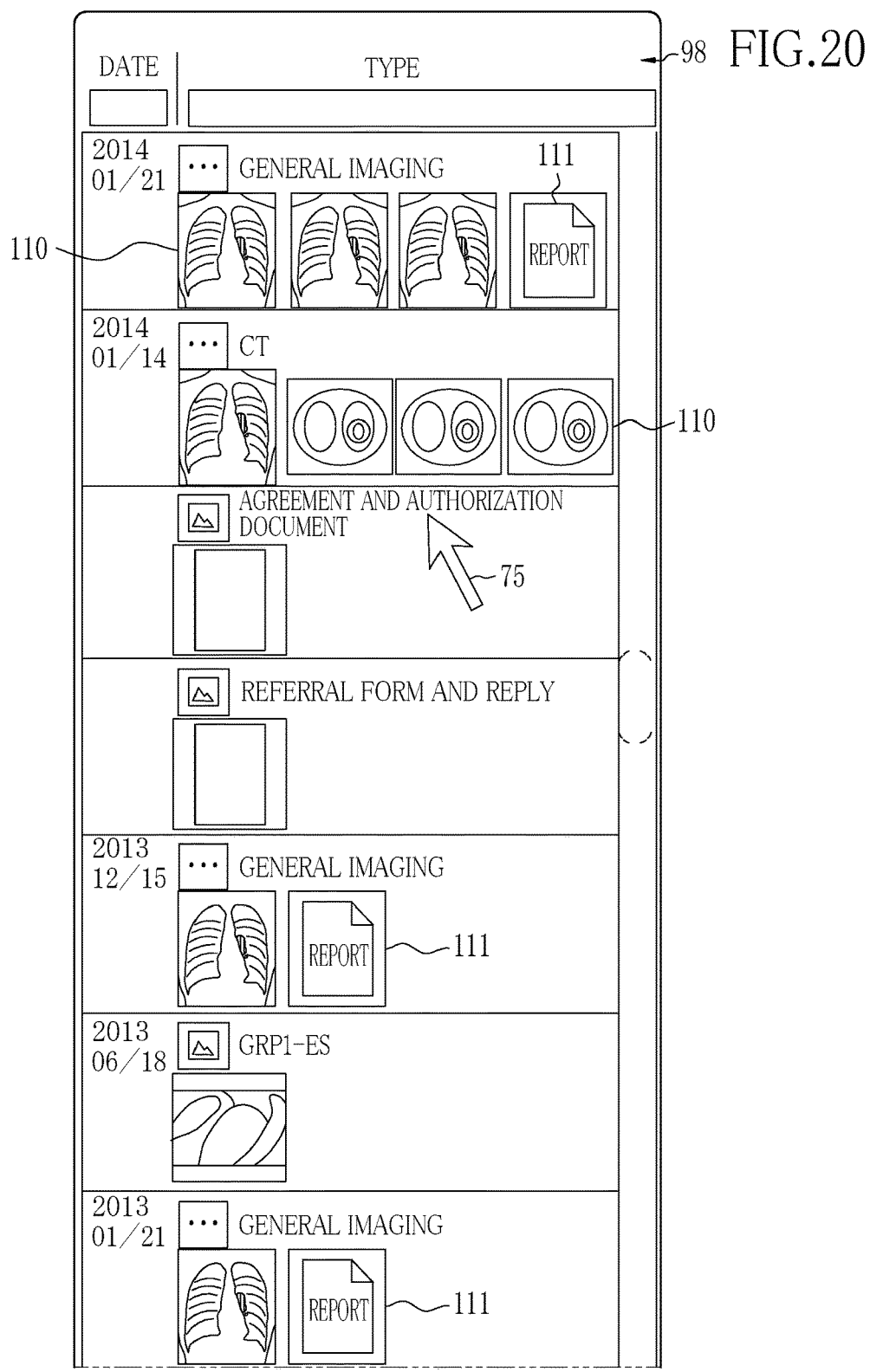
FIG. 20 illustrates an examination history display section.

In the examination history display section 98 shown in FIG. 20, the histories of various types of medical examinations are listed chronologically with the medical examination of the latest date and time listed on the top. In the history of each medical examination, time and date of the medical examination, a thumbnail icon 110 of the diagnostic image 25, and a link icon 111 for the medical report 26 are displayed. The history of the medical examination with the progress status "not-performed" is not displayed, and hence the icons 110 and 111 are not displayed in the examination history display section 98.

In the case where the thumbnail icon 110 is chosen with use of the cursor 75, the diagnostic image 25 corresponding to the chosen thumbnail icon 110 is displayed in the corresponding examination result display section. For example, in the case where the thumbnail icon 110 of an X-ray image is chosen, the X-ray image corresponding to the chosen thumbnail icon 110 is displayed in the DR result display section 92. In the case where the link icon 111 is chosen with use of the cursor 75, the medical report 26 corresponding to the chosen link icon 111 is displayed in the report display section 94. A command for choosing the icon 110 or 111 is issued as the edit request by the command issuer 42.

In the DS result display section 92, the US result display section 96, and the ES result display section 97, which are displayed at first in the second display screen 15B in response to the selection of the patient information with use of the cursor 75, the diagnostic images 25 captured in the latest medical examinations are displayed. In the ECG result display section 95 and the report display section 94, the ECG image captured in the latest ECG examination and the corresponding medical report 26 are displayed, respectively.

Upon receiving the edit request, which is issued in response to the choosing of the patient information, or the edit request, which is issued in response to the choosing of the link icon 111, from the command receiver 46, the screen edit information manager 47 determines that the medical staff logged in has finished confirming the medical report 26. In the case where the progress status of the item "examination" of the progress status information 50 corresponding to the medical staff logged in is "unconfirmed", the screen edit information manager 47 changes the progress status to "confirmed".

Hereinafter, by referring to a flowchart in FIG. 21, an operation of the above-described configuration is described. First, the medical staff operates the client terminal apparatus 12 to start the viewer software 40. Upon the startup of the viewer software 40, the GUI controller 41 and the command issuer 42 are constructed in the CPU 32B of the client terminal apparatus 12.

Figure 21:
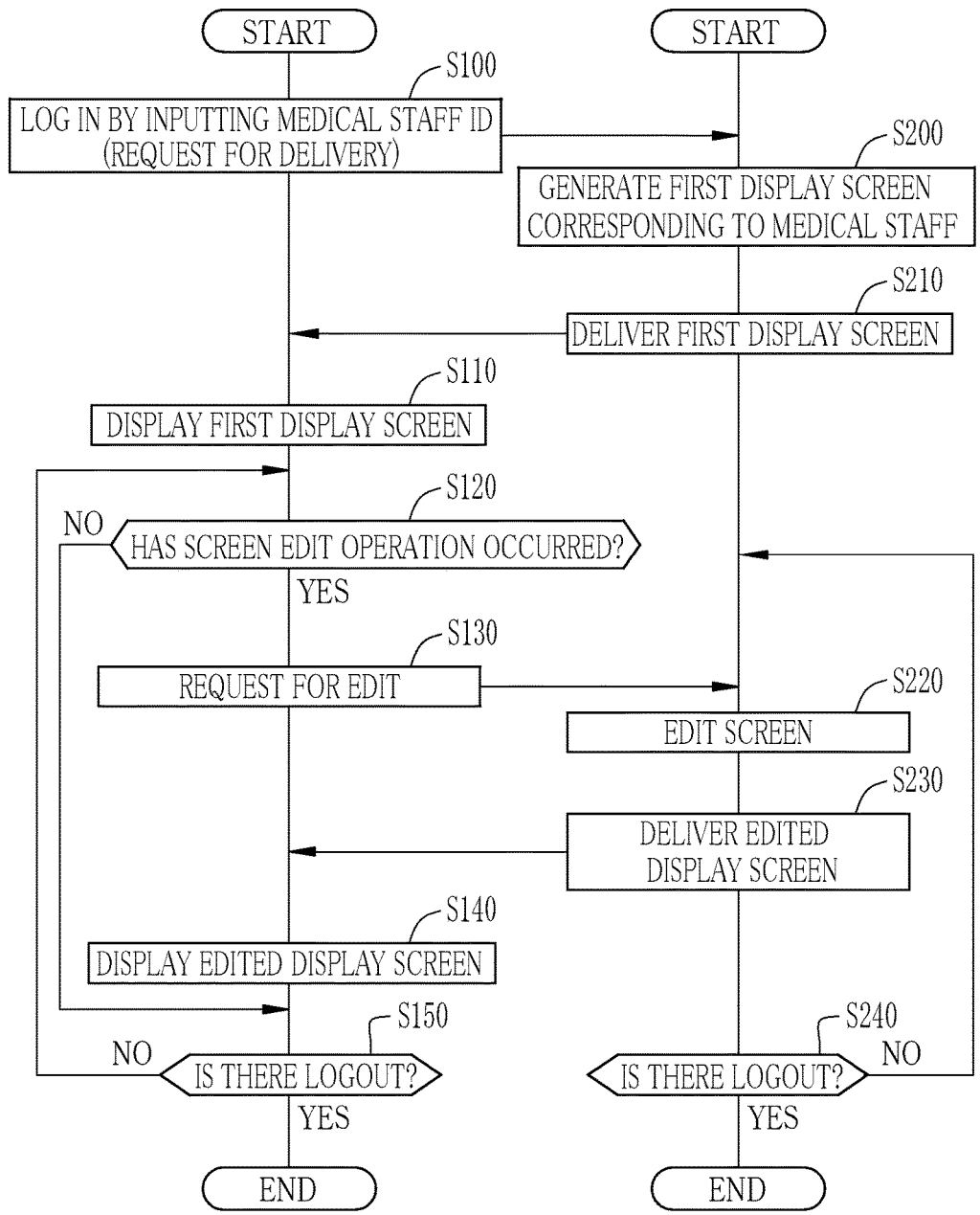
FIG. 21 is a flow chart illustrating a flow of processing performed by each functional part of the CPU of each of the medical support server apparatus and the client terminal apparatus.

In step S100 as shown in FIG. 21, the medical staff inputs the medical staff ID through the log-in screen, to view the first display screen 15A. Thereby, the command issuer 42 issues the delivery request for the first display screen 15A.

The operation program 45 starts up in the medical support server apparatus 11, so that the command receiver 46, the screen edit information manager 47, the screen editor 48, and the delivery controller 49 are constructed in the CPU 32A. Thereby, the medical support server apparatus 11 functions as the medical support apparatus.

The command receiver 46 of the medical support server apparatus 11 receives the delivery request issued from the command issuer 42 of the client terminal apparatus 12. The delivery request is transmitted to the screen edit information manager 47. The screen edit information manager 47 picks up (retrieves) the screen edit information 16 that is necessary for generating the first display screen 15A from the screen edit information DB 11A. For example, the screen edit information manager 47 retrieves the progress status information 50 necessary for generating the patient list 71. The screen edit information 16 retrieved by the screen edit information manager 47 is provided (transmitted) to the screen editor 48.

The screen editor 48 generates the first display screen 15A based on the screen edit information 16 provided by the screen edit information manager 47 (step S200). At this time, the screen editor 48 changes the display state of the small icon 82 in accordance with a change in progress status of the corresponding medical examination as illustrated in FIG. 17. As illustrated in FIG. 18, the display state of the general icon 81C is changed in accordance with a change in progress status of the corresponding medical care process other than the medical examination.

In the case where at least one of part of a plurality of items and part of a plurality of pieces of patient information cannot be contained within the first display screen 15A, namely, hidden, the screen editor 48 provides the horizontal scroll bar 78 or the vertical scroll bar 79 in the patient list 71, as shown in FIG. 13. In the case where the medical staff has not confirmed the medical report 26 that is the reporting of the result of various types of medical examinations whose progress statuses are displayed in the small icons 82 of each of the special icons 81B disposed at the item "examination" in the hidden section, the unconfirmed medical-care-process display section 80 for representing that there is a medical examination whose medical report 26 has not been confirmed is disposed in the first display screen 15A. The generated first display screen 15A is delivered to the client terminal apparatus 12 by the delivery controller 49 (step S210).

The GUI controller 41 displays the first display screen 15A on the display panel 34B of the client terminal apparatus 12 (step S110). The first display screen 15A displays the patient list 71, which includes the special icons 81B. In each special icon 81B, two or more small icons 82 are disposed. Each small icon 82 represents the progress status of the corresponding medical examination.

Since the unconfirmed medical-care-process display section 80 is displayed in first display screen 15A, the medical staff can perceive that there is a medical examination whose medical report 26 has not been confirmed yet, without performing the scrolling operation. Since the hidden section is not displayed without the scrolling operation, in the case where the special icon 81B disposed at the item "medical examination" whose medical report 26 is required to be confirmed is in the hidden section as shown in FIG. 13, the medical staff may not find the existence of the medical examination whose progress status is "unconfirmed" unless the unconfirmed medical-care-process display section 80 is displayed. However, it is possible to surely avoid such a situation by the unconfirmed medical-care-process display section 80. Accordingly, thanks to the icon 81, it is possible to surely avoid the situation that the display of the progress status of the medical care process is missed, and it is possible to smoothly proceed with the medical care process.

The unconfirmed medical-care-process display section 80 is inserted between the icons 81 of the patients arranged along the horizontal axis X, and displayed. Since the unconfirmed medical-care-process display section 80 is disposed at a position adjacent to the icon 81 of the target patient as described above, it is easy to perceive the patient having the unconfirmed medical care process.

The blocks 87 constituting the unconfirmed medical-care-process display section 80 are aligned and displayed at the head position of the items at the side of the patient information display section 77 in which a plurality of pieces of the patient information are arranged. Therefore, more blocks 87 can be displayed in the unconfirmed medical-care-process display section 80.

Under the constraint that the display area of the patient list 71 is limited in the horizontal axis X direction, the small icons 82, each of which represents the progress status of the corresponding medical examination, are displayed compactly in size in the special icon 81B. Thereby, the unnecessary increase in the width of the item display section 76 in the horizontal axis X direction is prevented. Thus, the need of the medical staffs to confirm as many progress statuses of the medical care processes as possible at a time without extra effort and time has been met.

The small icons 82 represent the progress statuses of the medical care processes of the same category (the medical examinations in this example). The small icons 82 are put together in one special icon 81B, so that the progress statuses of the medical care processes of the same category (various types of medical examinations) are confirmed at a glance. Thereby, the progress status of each medical examination is noticed easily as compared with that of the case where the icons representing the progress statuses of various medical examinations are scattered throughout the patient list 71. Thus, the perspicuity (clarity) of the progress statuses of the various medical examinations is improved. Since there are many types of medical examinations (e.g. imaging examinations, laboratory tests, and physiological tests), the merit of confirming the progress statuses at a glance can be made full use of.

The patient list 71 also displays the general icon 81C the same size as the special icon 81B. The general icon 81C represents the progress status of the medical care process other than the medical examination. The general icon 81C displays various types of text information about the medical care processes (e.g. the date and time of the medical care process performed, the scheduled date and time of the medical care process to be performed, the type of the medical care process, the medical staff who is scheduled to perform the medical care process or who has performed the medical care process, a reason for suspending the medical care process, and the like). The small icon 82 also displays the text information that denotes the type of the medical examination. Hence, the information about the medical care processes is conveyed sufficiently to the medical staffs, contributing to the efficiency of the team medicine.

The icons 81 may be composed of the special icons 81B only. In this case, however, it may become difficult to confirm the content of the medical care processes and comprehend the progress statuses. In this embodiment, the special icons 81B are limited to those representing the progress statuses of the medical care processes of the same category. The progress statuses of the remaining medical care processes are represented by the general icons 81C. Thereby, the patient list 71 makes it easy to grasp the progress statuses as a whole.

The small icon 82 represents the progress status "not-performed", "unconfirmed", or "confirmed". The progress status "not-performed" corresponds to the state in which the medical examination has not been performed. The progress status "unconfirmed" corresponds to the state in which the medical report 26 has been created and the medical examination has been performed but the medical report 26 has not been confirmed. The progress status "confirmed" corresponds to the state in which the medical report 26 has been confirmed. For example, in the case where the medical staff is a laboratory technologist and the progress status represented by the small icon 82 is "not-performed", the small icon 82 can prompt the laboratory technologist to perform the medical examination as soon as possible. In the case where the medical staff is a doctor and the progress status represented by the small icon 82 is "unconfirmed", the small icon 82 can prompt the doctor to confirm the medical report 26 as soon as possible.

The general icon 81C represents the progress status "not-started", "not-completed", or "completed". The progress status "not-started" corresponds to the state in which the medical care process has not been started. The progress status "not-completed" corresponds to the state in which the medical care process has been started but has not been completed. The progress status "completed" corresponds to the state in which the medical care process has been completed. In the case where the progress status represented by the general icon 81C is "not-started" or "not-completed", the general icon 81C can prompt the medical staff to start or complete the medical care process as soon as possible, in a manner similar to the small icon 82.

The general icon 81C and the small icon 82 are displayed only for the medical care processes that are scheduled to be performed. A medical care process that is not required to be performed is left as the blank space 83. Thereby, the medical care processes that are scheduled to be performed and those that are not required to be performed are shown at a glance. Consequently, errors such as performing an unnecessary medical care process can be prevented.

The patient list 71 is generated in accordance with the medical staff. The items displayed in the item display section 76, the patients displayed in the patient information display section 77, and the progress statuses of the medical care processes represented by the icons 81 vary according to the medical staff. Thereby, each medical staff is positively informed of the progress statuses of the medical care processes of the patients whom he/she is in charge of. Each medical staff becomes aware of what to prepare and what to do in the medical care processes and smoothly proceeds with the medical care processes.

The medical staff views the first display screen 15A, and confirms the progress status of each medical care process of each patient. The medical staff operates the patient type selection tab 72 or the like as necessary to further narrow down the patients displayed on the patient list 71 by the patient type, or selects the patient information displayed in the patient information display section 77 so as to display the second display screen 15B. In the case where such screen edit operation is performed (YES in step S120), the edit request is issued from the command issuer 42 (step S130).

The edit request, which is issued by the command issuer 42 of the client terminal apparatus 12, is accepted (received) by the command receiver 46 of the medical support server apparatus 11, and then transmitted to the screen edit information manager 47. The screen edit information manager 47 picks up (retrieves) the screen edit information 16 necessary for editing the screen from the screen edit information DB 11A. The screen edit information 16 retrieved by the screen edit information manager 47 is transmitted to the screen editor 48.

Based on the screen edit information 16 from the screen edit information manager 47, the screen editor 48 edits the screen (step S220). For example, in the case where the edit request from the command receiver 46 is an edit request for editing the second display screen 15B, the second display screen 15B is edited based on the various types of medical care data provided by the screen edit information manager 47. The delivery controller 49 delivers the edited first display screen 15A or the edited second display screen 15B to the client terminal apparatus 12 (step S230).

The GUI controller 41 of the client terminal apparatus 12 displays the edited first display screen 15A or the edited second display screen 15B on the display panel 34B (step S140). Each medical staff views the second display screen 15B to confirm the result of each medical examination and each medical report 26, which is the report of the result of the medical examination, at a glance. When or after the medical staff views the second display screen 15B, the screen edit information manager 47 changes the progress status of the item "examination" of the progress status information 50 to "confirmed" in the case where the progress status of the item "examination" corresponding to the medical staff viewing the second display screen 15B is "unconfirmed".

In the case where the edit request from the command receiver 46 is an edit request to narrow down the patients displayed in the patient list 71 by the patient type, the patient list 71 is generated in accordance with the patient type chosen. In the patient list 71 generated, the items displayed in the item display section 76, the patients displayed in the patient information display section 77, and the progress statuses of the medical care processes represented by the icons 81 vary according to the patient type. Thus, the progress statuses of the medical care processes corresponding to the patient type are smoothly comprehended.

The client terminal apparatus 12 repeats the above-described steps (steps S120 to S140) until the medical staff provides the command to logout (NO in step S150). In a like manner, the medical support server apparatus 11 repeats the above-described steps (steps S220 and S230) until the command receiver 46 receives the command to logout (NO in step S240).

Incidentally, FIG. 21 describes an example of a procedure for the case in which one client terminal apparatus 12 and one medical support server apparatus 11 are used. Actually, the medical support server apparatus 11 receives the delivery requests and the edit requests from two or more client terminals 12, generates the first display screens 15A of the client terminals 12, edits the first and second display screens 15A and 15B of the client terminals 12, and delivers the first and second display screens 15A and 15B to the client terminals 12 at the same time.

Second Embodiment

In the above first embodiment, in the case where the medical staff has not confirmed the medical report 26 that is the reporting of the result of various types of medical examinations whose progress statuses are represented by the small icons 82 of the special icon 81B disposed at the item of the examination in the hidden section, the unconfirmed medical-care-process display section 80 is always displayed. However, the unconfirmed medical-care-process display section 80 may not be displayed in a period after the medical report 26 is uploaded and before the predetermined time limit is reached, and the unconfirmed medical-care-process display section 80 may be displayed in the case where the medical report 26 has not been confirmed yet after the time limit has been reached.

Figure 22:
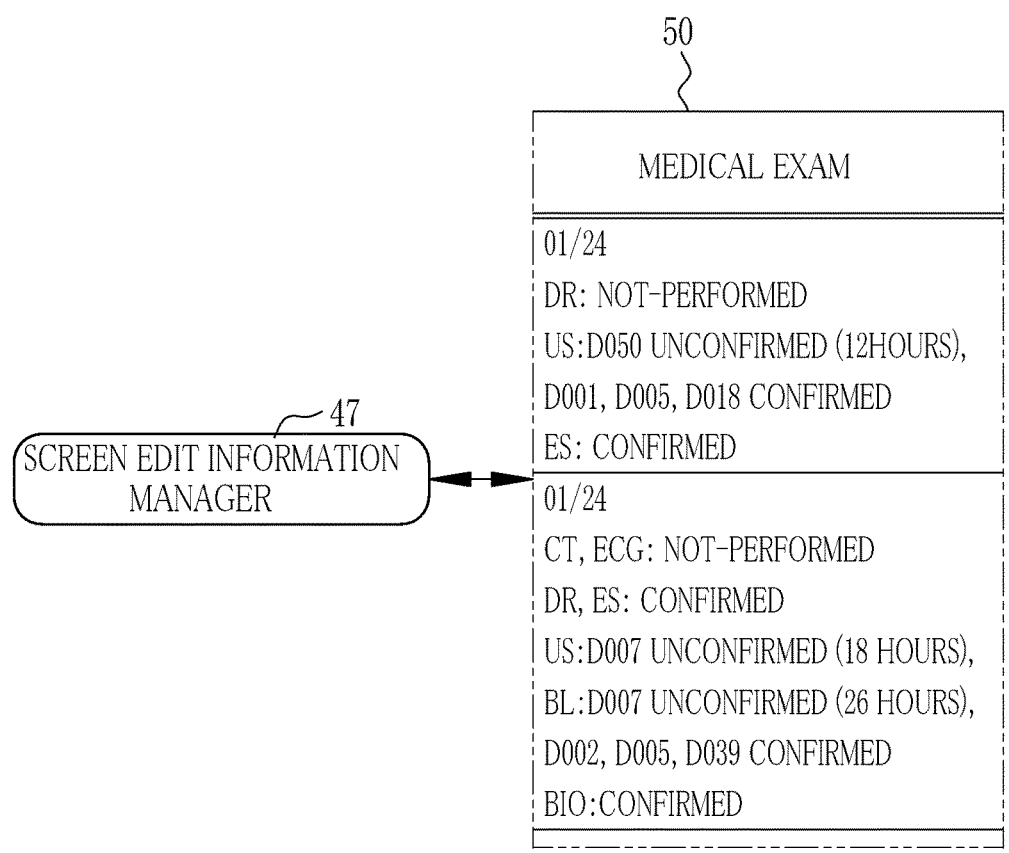
FIG. 22 illustrates that a time elapsed from when the progress status of the medical examination became "unconfirmed" is recorded in the progress status information by managing screen edit information.

In this case, as shown in FIG. 22, the screen edit information manager 47 measures elapsed time from a point of time when the progress status of each type of medical examination becomes "unconfirmed", and records the measured elapsed time in the item "examination" of the progress status information 50 at the timing of obtaining the medical care data from the server cluster 13 or another timing. The screen edit information manager 47 describes the measured elapsed time (e.g. "US: D050 unconfirmed (12 hours)", "BL: D007 unconfirmed (26 hours)") for the medical examinations whose progress statuses is "unconfirmed". The screen edit information manager 47 provides the screen edit information 16 containing the information of the elapsed time to the screen editor 48.

The screen editor 48 switches the unconfirmed medical-care-process display section 80 between the display state and the hidden state based on the information of the elapsed time provided from the screen edit information manager 47. An example, in which the medical staff ID inputted through the log-in screen is "D007" and the time limit is set to 24 hours, is explained hereinbelow.

Figure 23:
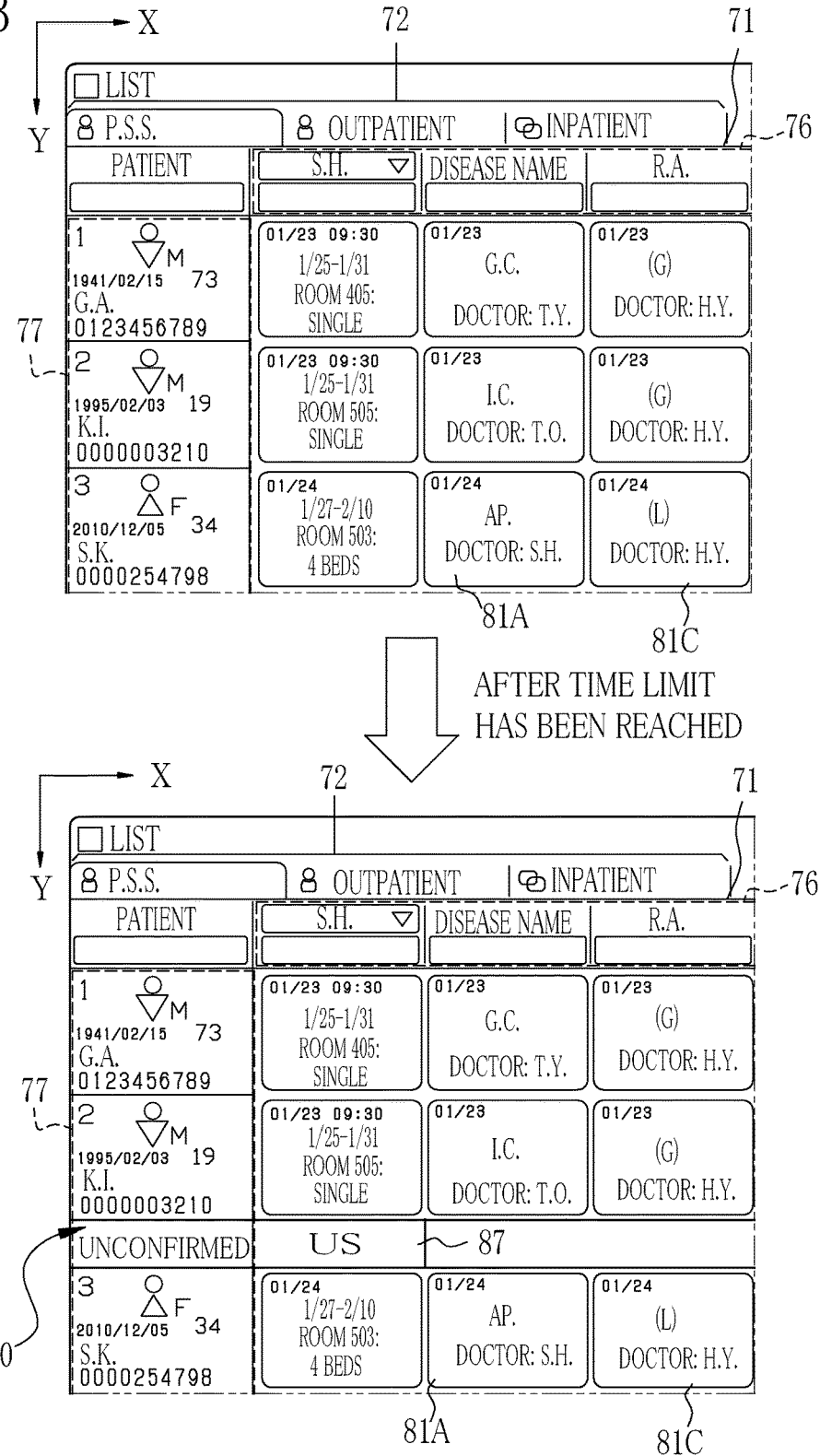
FIG. 23 illustrates a second embodiment in which an unconfirmed medical-care-process display section is switched between a display state and a hidden state in accordance with the elapsed time.

In the case where the medical staff logged in more than two hours ago from the state shown in FIG. 22, the elapsed time from a point of time when the progress status of the medical examination became "unconfirmed" does not exceed 24 hours, the unconfirmed medical-care-process display section 80 is not displayed as shown in an upper part from the arrow of FIG. 23. In contrast, in the case where when the medical staff logged in corresponds to the state shown in FIG. 22, the elapsed time from a point of time when the progress status of the blood test became "unconfirmed" is 26 hours, namely, exceeds 24 hours as the time limit, and therefore unconfirmed medical-care-process display section 80 having the block 87 on which the characters "BL" is shown is displayed as shown by a lower part from the arrow of FIG. 23.

Until the time limit is reached, the unconfirmed medical-care-process display section 80 is not displayed, and therefore the visibility of the patient list 71 can be secured. In the case where the time limit has been reached but the medical report 26 has not been confirmed yet, the unconfirmed medical-care-process display section 80 is displayed. Therefore, in comparison with the above first embodiment in which the unconfirmed medical-care-process display section 80 is always displayed, the medical staff can perceive more strongly that the medical report 26 is required to be confirmed promptly.

Incidentally, the setting of the time limit may be changed in accordance with the type of the patient or the type of the medical staff. For example, the time limit for the outpatient may be set to one hour, the time limit for the patient scheduled for surgery and inpatient may be set to 24 hours, the time limit for the doctor and laboratory technologist may be set to 12 hours, and the time limit for the nurse and dietician may be set to 24 hours. Alternatively, the setting of the time limit may be changed in accordance with the type of the medical examination. For example, the time limit for the imaging examination may be set to 12 hours, and the time limit for the laboratory test and the physiological test may be set to 24 hours.

According to the above first embodiment, as shown in FIG. 14, the unconfirmed medical-care-process display section 80 remains to be displayed even when the scrolling operation is performed and the hidden section is displayed. However, the unconfirmed medical-care-process display section 80 may be not displayed when the scrolling operation is performed and the hidden section is displayed.

Figure 24:
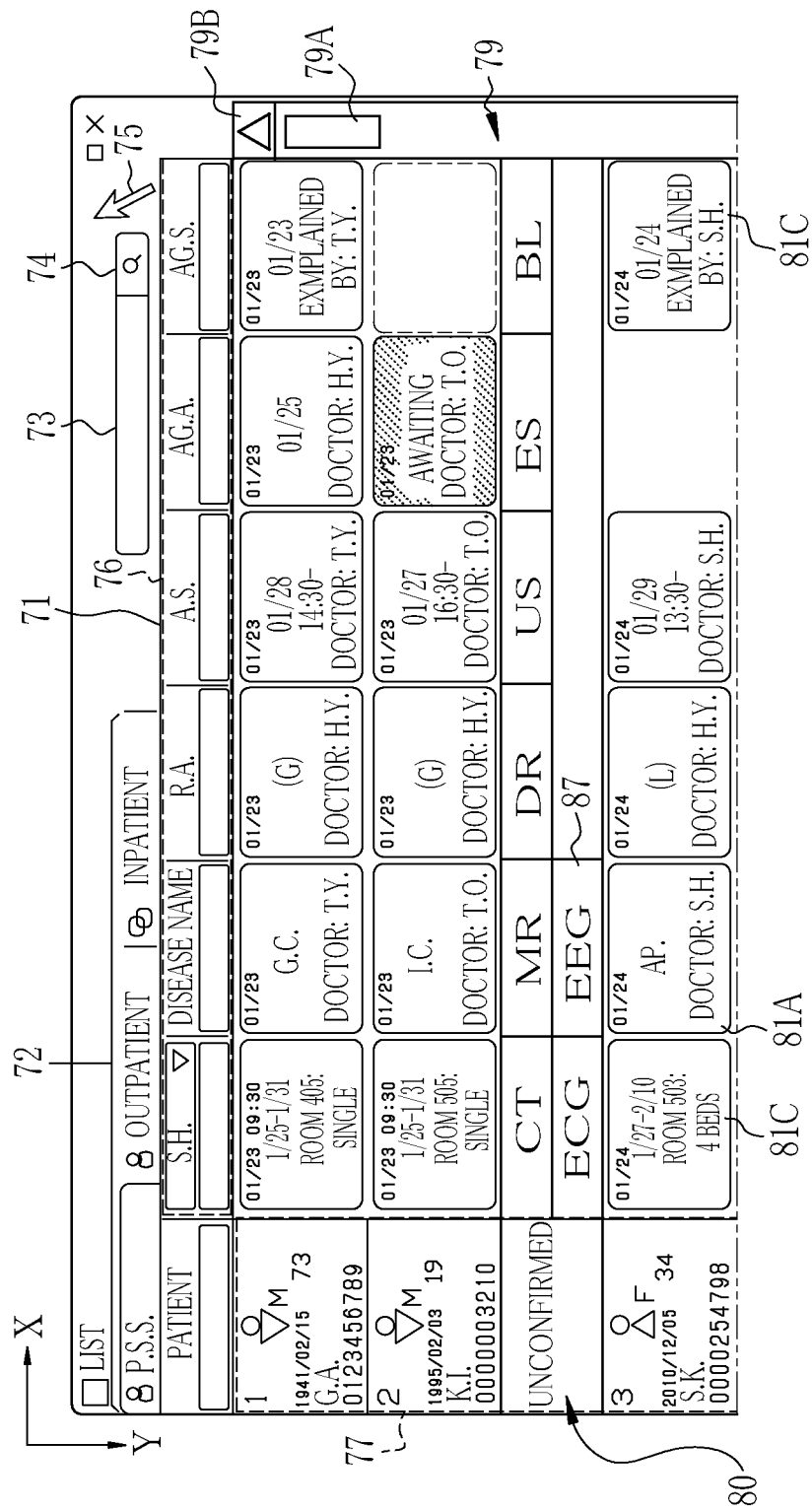
FIG. 24 illustrates an example in which the blocks are displayed by being returned to be arranged in one or more lines.

Incidentally, the size of the block 87 is not limited to one exemplified in the above first embodiment. For example, the width of the block 87 in the horizontal axis X direction may not be approximately the same as that of the icon 81. In the case where there are many medical examinations whose progress statuses are "unconfirmed" and some of the blocks 87 aligned in the horizontal axis X direction are not contained within the display section and enter the hidden section, the width of each the blocks 87 in the horizontal axis X direction may be decreased such that all the blocks 87 are contained within the display section. Alternatively, the blocks 87 may not be aligned in one line. The blocks 87 may be displayed by being returned to be arranged in one or more lines, as shown in FIG. 24, for example.

Figure 25:
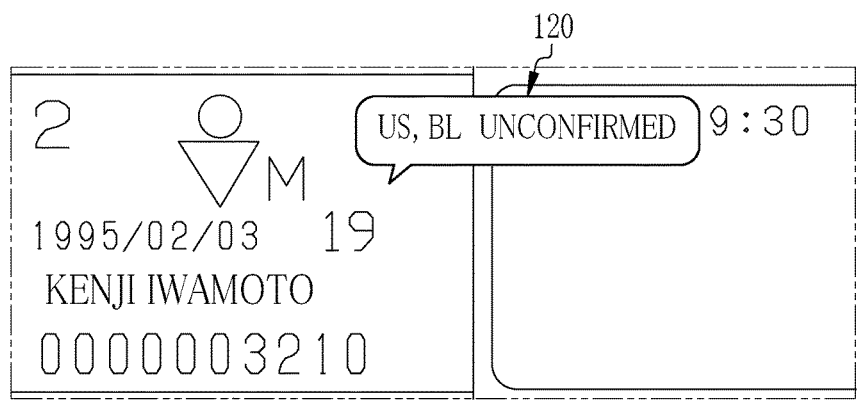
FIG. 25 illustrates another example of the unconfirmed medical-care-process display section.

The unconfirmed medical-care-process display section is not limited to the unconfirmed medical-care-process display section 80 consisting of the blocks 87 aligned in the horizontal axis X direction as in the case of the above first embodiment. For example, the unconfirmed medical-care-process display section may be an unconfirmed medical-care-process display section 120 as shown in FIG. 25. The unconfirmed medical-care-process display section 120 is a speech balloon mark in which the medical examination whose progress status is "unconfirmed" is displayed. In short, it is sufficient that the unconfirmed medical-care-process display section can represent that there is an unconfirmed medical care process which has not been confirmed yet, and the display mode of the unconfirmed medical-care-process display section may not be the one described in the above first embodiment.

The display position of the unconfirmed medical-care-process display section is not limited to between the icons 81 for the patients arranged along horizontal axis X as described in the above first embodiment. The unconfirmed medical-care-process display section may be displayed in the patient information display section 77 as in the case of the unconfirmed medical-care-process display section 120 shown in FIG. 25, and may be displayed in a position different from the patient list display section 67.

The progress statuses represented by the general icon 81C are not limited to three types, "not-started", "not-completed", and "completed" described in the first embodiment. The progress statuses represented by the small icon 82 are not limited to three types, "not-performed", "unconfirmed", and "confirmed" described in the first embodiment. For example, the progress status "not-completed" may be a case where the medical care process is suspended due to an obstacle or uncontrollable circumstances (e.g. the item "pre-operative summary" corresponding to the patient ID "0000003210" in FIG. 7, that is, the medical care process is suspended because another disease has been found and the patient is having medical treatment for the disease found), or a case where the medical care process is suspended without obstacle (e.g. simply due to waiting for the patient's submission of the agreement to surgery). The progress status "not-completed" may be separated into "suspended" (suspended due to an obstacle or uncontrollable circumstances) and "awaiting" (suspended without obstacle).

With regard to the progress status represented by the small icon 82, the progress status "examination is underway", which corresponds to a period after the order is confirmed (step S11) and before the report is uploaded (step S16) shown in FIG. 8, may be added, in addition to the above-described statuses "not-performed", "unconfirmed", and "confirmed". The progress status "report creation", which corresponds to a period after the examination result is uploaded (step S14) and before the report is uploaded (step S16) shown in FIG. 8, may be used. The progress status "image is unconfirmed", which corresponds to a period after the examination result is uploaded (step S14) and before the report is created (step S15), may be used.

The progress status represented by the small icon 82 may be changed according to the medical staff type. The display of the progress status may be changed according to each medical staff. In a top portion of FIG. 26, in the case of a doctor who issues an order, for example, the progress status corresponding to a period after the order is issued (step S10) and before the order is confirmed (step S11) is referred to as "not-performed". The progress status corresponding to a period after the order is confirmed (step S11) and before the examination result is uploaded (step S14) is referred to as "examination is underway". The progress status corresponding to a period after the examination result is uploaded (step S14) and before the report is uploaded (step S16) is referred to as "report creation". The progress status corresponding to a period after the report is uploaded (step S16) and before the report is confirmed (step S17) is referred to as "unconfirmed". The progress status corresponding to a period after the report is confirmed (step S17) is referred to as "confirmed".

In the case of the medical staff type "radiological doctor", who creates the medical report 26, the progress statuses "not-performed" and "examination is underway" are the same as those of the medical staff type "doctor". The progress status corresponding to a period after the upload of the examination result (step S14) and before the creation of the report (step S15) is referred to "image unconfirmed". The progress status corresponding to a period after the creation of the report (step S15) is referred to as "confirmed". As described above, the progress status represented by the small icon 82 is changed according to the medical staff type, so that the progress status displayed is precise and suitable for the corresponding medical staff type. The progress status represented by the general icon 81C may be changed according to the medical staff type, in a like manner.

Incidentally, although the medical report 26 as the reporting of the result of the medical examination is exemplified as the result of the medical care process required to be confirmed by the medical staff, instead of or in addition to the medical report 26, the result of the medical examination may be the result of the medical care process required to be confirmed by the medical staff. Regarding the result of the medical examination, the imaging examination corresponds to the diagnostic image 25, and each of the laboratory test and physiological test corresponds to test value as described above.

Further, although the medical examination is exemplified as the medical care process whose result is required to be confirmed by the medical staff in the first embodiment, the progress status "unconfirmed" and the progress status "confirmed" may be prepared for the medical care process other than the medical examination, and the medical care process other than the medical examination may be the target to be displayed in the unconfirmed medical-care-process display section. As the medical care process other than the medical examination, whose result is required to be confirmed by the medical staff, there are various types of agreements such as the agreement to anesthesia and various types of plan documents such as the clinical path.

In the first embodiment, the special icon 81B is described by way of example. The special icon 81B in the first embodiment contains the small icons 82, which represent the progress statuses of the medical care processes of the same category (that is, "medical examination"). Two or more small icons 82 contained within one special icon 81B may not necessarily represent the progress statuses of the medical care processes of the same category. However, in the case where the small icons 82 do not represent the progress statuses of the medical care processes of the same category, the display of the progress statuses may become complicated because the small icons 82 displayed have no commonality among them. Therefore, it is preferred that two or more small icons 82 contained within one special icon 81B represent the progress statuses of the medical care processes of the same category.

Incidentally, another example of the medical care processes of the same category may be the medical care processes: "agreement to anesthesia" and "agreement to surgery". The medical care processes of the same category may be the medical care processes for measuring the vital signs (e.g. the heart rate, the pulse rate, the blood pressure, the body temperature, and the like of a patient).

In the first embodiment, the second display screen 15B is displayed in the case where one of the pieces of the patient information of the patient information display section 77 is chosen with use of the cursor 75. Alternatively, the general icon 81C or the small icon 82 may be chosen with use of the cursor 75. The second display screen 15B may be displayed in response to the choosing of the general icon 81C or the small icon 82 with use of the cursor 75.

Figure 26:
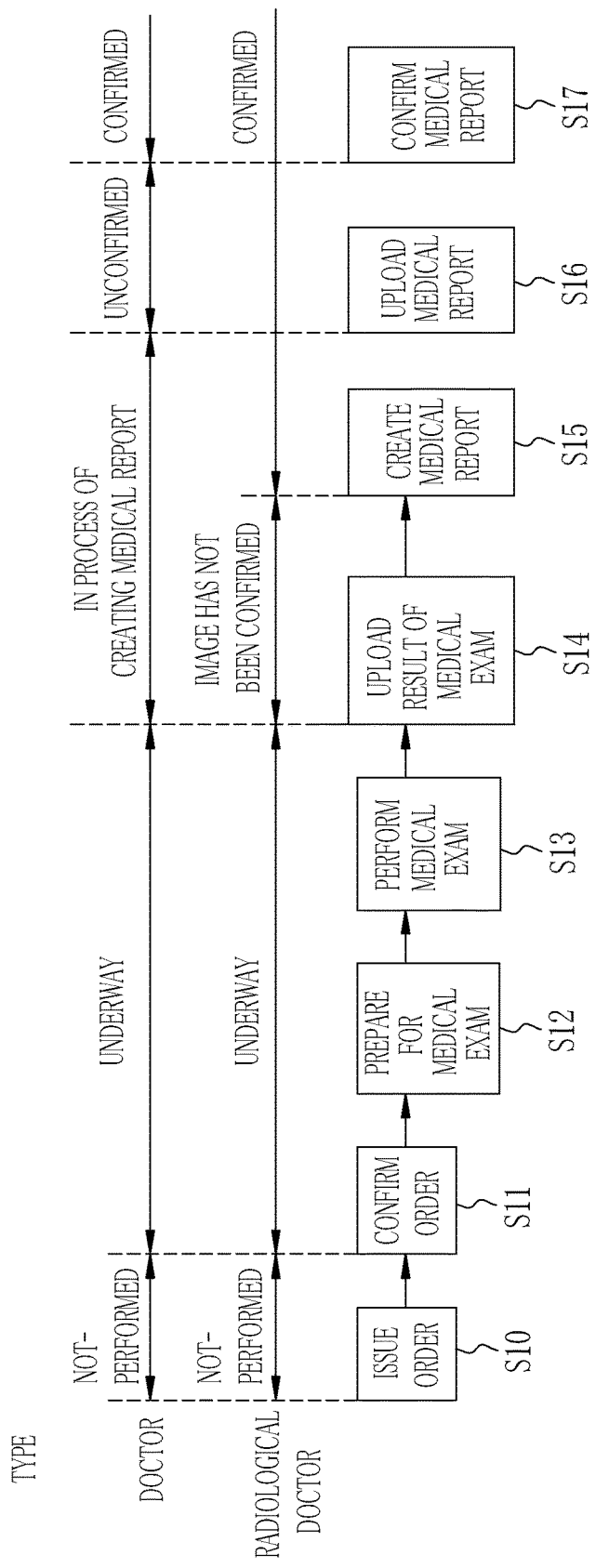
FIG. 26 is an explanatory view illustrating an example in which the progress status is changed according to medical staff types.

In addition to the doctors, the laboratory technologists, the nurses, and the dieticians, the medical staffs may include physical therapists who help the patients to rehabilitate and pharmacists who prescribe medicine and instruct the patients how to take it. As illustrated in FIG. 26 by way of example, the types of the medical staffs may be further subdivided in accordance with the tasks or job types. For example, the medical staff type "doctor" may be subdivided into "clinician" who diagnoses and treats the patient and "radiological doctor" who creates the medical report 26. For example, the medical staff type "laboratory technologist" may be subdivided into "radiologic technologist" and "sonographer".

In the first embodiment, the items displayed in the patient list 71, the patient identification information, and the progress statuses vary according to the patient of whom the corresponding medical staff is in charge and the medical care process. Instead, at least one of the displayed items, the patient identification information, and the progress statuses may vary according to the patient of whom the corresponding medical staff is in charge and the medical care process. The items displayed in the patient list 71, the patient identification information, and the progress statuses vary according to the patient type. Instead, at least one of the items displayed, the patient identification information, and the progress statuses may vary according to the patient type.

The medical examinations whose progress statuses are represented by the small icons 82 do not have to include all of the imaging examination, laboratory test, and physiological test. At least one of the medical examinations may be displayed by using the small icon 82. The patient type may include "home care patient", who is treated at home.

In the first embodiment, the medical support apparatus according to an aspect of the present invention is described as the medical support server apparatus 11, which delivers the first display screen 15A to the client terminal apparatus 12 in response to the delivery request. Alternatively, as illustrated in FIG. 27, the client terminal apparatus 12 may function as the medical support apparatus. Incidentally, in FIG. 27, the parts similar to or the same as those in the first embodiment are designated by the same reference numerals as those in the first embodiment and the descriptions thereof are omitted.

The differences between the example illustrated in FIG. 27 and the above first embodiment are that (1) the operation program 45 is stored in the storage device 30B of the client terminal apparatus 12 and the CPU 32B of the client terminal apparatus 12 executes the operation program 45, so that the CPU 32B functions as the screen edit information manager 47 and the screen editor 48 and (2) the screen edit information 16 is stored in the storage device 30B.

In this case, the command issuer 42 issues various types of processing requests to the screen edit information manager 47. The screen edit information manager 47 directly accesses the server cluster 13 to retrieve the medical care data. Based on the retrieved medical care data, the screen edit information manager 47 updates the progress status information 50 and the storage location information 51 in the storage device 30B.

The screen editor 48 generates the first display screen 15A based on the screen edit information 16 in the storage device 30B, and transmits the first display screen 15A to the GUI controller 41. The GUI controller 41 allows the display panel 34B to display the first display screen 15A. Based on the edit request issued by the command issuer 42, the screen editor 48 edits the display contents of the first display screen 15A and the second display screen 15B. Thus, the medical support apparatus is not limited to the medical support server apparatus 11 described in the first embodiment. For example, the client terminal apparatus 12 may be used as the medical support apparatus as illustrated in FIG. 27.

In the first embodiment, the screen edit information manager 47 issues the retrieval request, which requests the retrieval of the medical care data, to the server cluster 13 at regular time intervals. In response to the retrieval request, the screen edit information manager 47 obtains the medical care data transmitted from the server cluster 13. The present invention is not limited thereto. The screen edit information manager 47 may issue the retrieval request for the medical care data at the timing at which the first display screen 15A and the second display screen 15B are generated and edited. In this case, the medical support server apparatus 11 may not have the screen edit information DB 11A, and generates the progress status information 50 and the storage location information 51 of the screen edit information 16 every time the medical care data, which is transmitted from the server cluster 13, is obtained. The retrieval request may not be issued by the screen edit information manager 47. For example, the updated medical care data may be automatically transmitted from the server cluster 13 every time the medical care data is updated.

The medical support server apparatus 11 may carry out apart of the functions of the medical support apparatus, and the client terminal apparatus 12 may carry out another part of the functions of the medical support apparatus. For example, the first display screen 15A may be generated by the medical support server apparatus 11 and edited by the client terminal apparatus 12. In this case, a computer system composed of the client terminal apparatus 12 and the medical support server apparatus 11 functions as the medical support system. The medical support apparatus and the medical support system according to aspects of the present invention are implemented in various embodiments.

The hardware configuration of the computer system such as that of the medical support server apparatus 11 and the client terminal apparatus 12 may be modified in various ways. For example, the medical support server apparatus 11 may be composed of two or more server computers that are independent from each other as hardware. Thus, the hardware configuration of the computer system may be changed as necessary in accordance with the required performance (e.g. throughput (processing capacity), safety, and reliability).

In addition to the hardware, the application programs (e.g. the operation program 45) may be backed up or distributed and stored in two or more storage devices, to ensure safety and reliability.

In the above first embodiment, the medical support server apparatus 11 and the client terminal apparatus 12 are used in one medical facility, by way of example. For example, one medical support server apparatus 11 may be installed in a data center located outside the medical facility so that the client terminals 12 in two or more medical facilities are capable of using the application services (e.g. the data delivery service) of the medical support server apparatus 11.

In this case, the medical support server apparatus 11 is connected in a communicable manner to the client terminals 12, which are installed in the medical facilities, through a WAN (Wide Area Network) (e.g. Internet, public communication network, or the like). The medical support server apparatus 11 accepts the processing requests from the client terminals 12 of the medical facilities, and offers the application services such as delivery of the first display screens 15A to the respective client terminals 12.

The data center and the medical support server apparatus 11 may be installed in or managed by one of the medical facilities or a service company independent from the medical facility. In the case where a WAN (e.g. a network or the like) is used, it is preferred to construct a VPN (Virtual Private Network) or to use a communication protocol with a high security level (e.g. HTTPS (Hypertext Transfer Protocol Secure) or the like).

The present invention is not limited to the above first embodiment. Various changes and modifications are possible so long as they are within the scope of the present invention. Various embodiments may be combined with the modified embodiments.

What is claimed is:

1. A medical support apparatus comprising:
at least one processor programmed to operate as:
a screen generator to generate a display screen for patient care, the display screen displaying a patient list in which icons are arranged in a matrix in a two-dimensional area with an item arrangement axis and a patient identification information arrangement axis, a plurality of medical care processes performed on patients in the patient list by medical staffs being arranged as items in the item arrangement axis, patient identification information for identifying the patients in the patient list being arranged in the patient identification information arrangement axis, wherein the icons represent progress statuses of the displayed medical care processes on a patient-by-patient basis in the patient list; and
a screen display controller to allow a subset of items and icons corresponding to the subset of items to be designated as hidden icons, wherein the hidden icons are not constantly displayed on the display screen for patient care, the screen display controller allowing display of the hidden icons in response to a scrolling operation, the screen display controller further displaying an unconfirmed medical-care-process display section on the display screen for patient care, corresponding to a condition that there is an unconfirmed medical care process when there is at least one icon corresponding to the unconfirmed medical care process included among the hidden icons, wherein the unconfirmed medical care process has a result which has not been confirmed by the medical staff.

2. The medical support apparatus as defined in claim 1, wherein the unconfirmed medical-care-process display section is obtained by arranging blocks corresponding the icons representing the progress statuses of the unconfirmed medical care processes.

3. The medical support apparatus as defined in claim 2, wherein the unconfirmed medical-care-process display section is inserted between the icons of patients arranged along the item arrangement axis, and displayed.

4. The medical support apparatus as defined in claim 3, wherein the blocks are aligned and displayed at a head position of the items at a side in which the patient identification information are arranged.

5. The medical support apparatus as defined in claim 1, wherein the medical care process which is required to be confirmed is a medical examination.

6. The medical support apparatus as defined in claim 5, wherein the unconfirmed medical-care-process display section is displayed in the case where a preliminarily-set time limit has been reached after a result of the medical examination or a medical report as a reporting of the result of the medical examination is uploaded but the result of the medical examination or the medical report has not been confirmed.

7. The medical support apparatus according to claim 5, wherein the medical examination is at least one of imaging examination, laboratory test, and physiological test.

8. The medical support apparatus according to claim 1, wherein the icon is displayed only for the medical care process scheduled to be performed.

9. The medical support apparatus according to claim 1, wherein
the patient list is generated according to the medical staffs, and
at least one of the item to be displayed, the patient identification information, and the progress status in the patient list varies according to the patients taken care of by the medical staffs and the medical care processes.

10. The medical support apparatus according to claim 1, wherein
the patient list is generated according to patient types, and
at least one of the item to be displayed, the patient identification information, and the progress status in the patient list varies according to the patient types.

11. The medical support apparatus according to claim 10, wherein the patient types include a patient scheduled for surgery who is scheduled to have surgery, an outpatient who visits a medical facility, and an inpatient who is admitted to the medical facility.

12. The medical support apparatus according to claim 1, wherein the hidden icons are assigned two-dimensionally and individually to patient identification information and the plurality of medical care processes in the matrix.

13. The medical support apparatus according to claim 1, wherein the hidden icon comprises a speech balloon describing the unconfirmed medical care process.

14. The medical support apparatus as defined in claim 1, wherein the icons include a plurality of first icons each of which has a plurality of second icons disposed therein, each of the plurality of second icons being smaller than each of the plurality of first icons and representing a progress status of a medical examination.

15. The medical support apparatus as defined in claim 14, wherein one to three letters representing the medical examination are displayed in each of the plurality of second icons.

16. The medical support apparatus as defined in claim 15, wherein a display state of the letters and frame lines of each of the plurality of second icons varies according to a change in the progress status of the medical examination.

17. An operation method of a medical support apparatus comprising:
using at least one processor to perform;
a screen generating step for generating a display screen for patient care, the display screen displaying a patient list in which icons are arranged in a matrix in a two-dimensional area with an item arrangement axis and a patient identification information arrangement axis, a plurality of medical care processes performed on patients in the patient list by medical staffs being arranged as items in the item arrangement axis, patient identification information for identifying the patients in the patient list being arranged in the patient identification information arrangement axis, wherein the icons represent progress statuses of the displayed medical care processes on a patient-by-patient basis in the patient list; and
a screen display controlling step for allowing a subset of the items and icons corresponding to the subset of items to be designated as hidden icons, wherein the hidden icons are not constantly displayed on the display screen for patient care, the screen display further displaying, in response to a scrolling operation, an unconfirmed medical-care-process display section on the display screen for patient care, corresponding to a condition that there is an unconfirmed medical care process when there is at least one icon corresponding to the unconfirmed medical care process included among the hidden icons, wherein the unconfirmed medical care process has a result which has not been confirmed by the medical staff.

18. A medical care support system composed of a medical support apparatus, a client terminal apparatus, and a network that connects the medical support apparatus and the client terminal apparatus in a communicable manner, the medical care support system comprising:
at least one generator programmed to operate as:
a screen generator to generate a display screen for patient care, the display screen displaying a patient list in which icons are arranged in a matrix in a two-dimensional area with an item arrangement axis and a patient identification information arrangement axis, a plurality of medical care processes performed on patients in the patient list by medical staffs being arranged as items in the item arrangement axis, patient identification information for identifying the patients in the patient list being arranged in the patient identification information arrangement axis, wherein the icons represent progress statuses of the displayed medical care processes on a patient-by-patient basis in the patient list; and
a screen display controller to allow a subset of the items and icons corresponding to the subset items to be designated as hidden icons, wherein the hidden icons are not constantly displayed on the display screen for patient care, the screen display controller allowing display of the hidden icons in response to a scrolling operation, the screen display controller further displaying an unconfirmed medical-care-process display section on the display screen for patient care, corresponding to a condition that there is an unconfirmed medical care process when there is at least one icon corresponding to the unconfirmed medical care process included among the hidden icons, herein the unconfirmed medical care process has a result which has not been confirmed by the medical staff.

* * * * *